(12) United States Patent
Ma et al.

(10) Patent No.: US 9,040,738 B2
(45) Date of Patent: May 26, 2015

(54) INTERMEDIATE COMPOUNDS OF TAMIFLU, METHODS OF PREPARATION AND USES THEREOF

(75) Inventors: Dawei Ma, Shanghai (CN); Shaolin Zhu, Shanghai (CN); Shouyun Yu, Shanghai (CN); You Wang, Shanghai (CN); Qianghui Zhou, Zhejiang Province (CN)

(73) Assignees: SHANGHAI INSTITUTE OF ORGANIC CHEMISTRY, CHINESE ACADEMY OF SCIENCES, Shanghai (CN); LIANHE CHEMICAL TECHNOLOGY CO., LTD, Taizhou, Zhejiang (CN); LIANHE CHEMICAL TECHNOLOGY (TAIZHOU) CO., LTD, Taizhou, Zhejiang (CN)

( * ) Notice: Subject to any disclaimer, the term of this patent is extended or adjusted under 35 U.S.C. 154(b) by 305 days.

(21) Appl. No.: 14/123,870

(22) PCT Filed: Dec. 17, 2010

(86) PCT No.: PCT/CN2010/079936
§ 371 (c)(1),
(2), (4) Date: Feb. 28, 2014

(87) PCT Pub. No.: WO2011/076086
PCT Pub. Date: Jun. 30, 2011

(65) Prior Publication Data
US 2014/0221662 A1   Aug. 7, 2014

(30) Foreign Application Priority Data
Dec. 23, 2009   (CN) .......................... 2009 1 0200558

(51) Int. Cl.
| | |
|---|---|
| C07C 205/00 | (2006.01) |
| C07C 319/12 | (2006.01) |
| C07C 233/31 | (2006.01) |
| C07C 271/18 | (2006.01) |
| C07D 209/48 | (2006.01) |
| C07D 213/73 | (2006.01) |
| C07D 401/04 | (2006.01) |
| C07D 403/04 | (2006.01) |
| C07C 227/14 | (2006.01) |
| C07C 227/16 | (2006.01) |
| C07C 229/66 | (2006.01) |
| C07D 207/14 | (2006.01) |
| C07C 323/61 | (2006.01) |

(52) U.S. Cl.
CPC .......... C07C 319/12 (2013.01); *C07B 2200/07* (2013.01); C07C 233/31 (2013.01); C07C 271/18 (2013.01); *C07C 2101/14* (2013.01); *C07C 2101/16* (2013.01); C07D 209/48 (2013.01); C07D 213/73 (2013.01); C07D 401/04 (2013.01); C07D 403/04 (2013.01); C07C 227/14 (2013.01); C07C 227/16 (2013.01); C07C 229/66 (2013.01); C07D 207/14 (2013.01); C07C 323/61 (2013.01)

(58) Field of Classification Search
CPC ...................................................... C07D 213/73
USPC ......................................................... 560/125
See application file for complete search history.

(56) References Cited

U.S. PATENT DOCUMENTS

2008/0009639 A1   1/2008   Radatus et al.

FOREIGN PATENT DOCUMENTS

| | | | | |
|---|---|---|---|---|
| CN | 101735140 A | | 6/2010 | |
| CN | 102127003 A | | 7/2011 | |
| WO | WO 2009145263 | * | 3/2009 | ........... C07D 209/48 |
| WO | WO 2009/078813 A1 | | 6/2009 | |

OTHER PUBLICATIONS

Weng et al. Journal of Organic Chemistry (2010), 75(9), 3125-3128.*
Zhu et al. Angew. Chem. Int. Ed. 2010, 49, 4656-4660.*
Vicario et al. Synthesis 2007, 2065-2092, pp. 2067-2068. For.*
Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity," *J. Am. Chem. Soc.*, 1997, vol. 119, pp. 681-690.
Yeung et al., "A Short Enantioselective Pathway for the Synthesis of the Anti-Influenza Neuramidase Inhibitor Oseltamivir from 1,3-Butadiene and Acrylic Acid," *J. Am. Chem. Soc.*, 2006, vol. 128, pp. 6310-6311.
Trost et al., "A Concise Synthesis of (-)-Oseltamivir;" *Angew. Chem. Int. Ed.*, 2008, vol. 47, pp. 3759-3761.
Ishikawa et al., "High-Yielding Synthesis of the Anti-Influenza Neuramidase Inhibitor (-)-Oseltamivir by Three "One-Pot" Operations," *Angew. Chem. Int. Ed.*, 2009, vol. 48, pp. 1304-1307.
Dalko et al., "Enantioselective Organocatalysis," *Angew. Chem. Int. Ed.*, 2001, vol. 40, pp. 3726-3748.
Vicario et al., "Organocatalytic Enantioselective Michael and Hetero-Michael Reactions," *Synthesis*, Mar. 7, 2007, No. 14, pp. 2065-2092.
Enders et al., "Control of Four Stereocentres in a Triple Cascade Organocatalytic Reaction," *Nature*, Jun. 15, 2006, vol. 441, pp. 861-863.
Moualla et al., "Voreloxin," *Drugs of the Future*, 2009, vol. 34, No. 5, pp. 363-374.
Zhu et al., "Organocatalytic Michael Addition of Aldehydes to Protected 2-Amino-1-Nitroethenes: The Practical Syntheses of Oseltamivir (Tamiflu) and Substituted 3-Aminopyrrolidines," *Angew. Chem. Int. Ed.*, 2010, vol. 49, pp. 4656-4660.

(Continued)

Primary Examiner — Nizal Chandrakumar
(74) Attorney, Agent, or Firm — Oliff PLC

(57) ABSTRACT

Chiral amino compounds, methods of preparation and uses thereof. Tamiflu can be obtained from the said compounds. Multi-substituted chiral tetrahydropyrrolyl amine which can be used as intermediate compounds of medicament can also be produced by the said compounds.

16 Claims, No Drawings

(56) References Cited

OTHER PUBLICATIONS

International Search Report issued in International Patent Application No. PCT/CN2010/079936 dated Mar. 24, 2011 (with translation).

Written Opinion issued in International Patent Application No. PCT/CN2010/079936 dated Mar. 24, 2011 (with translation).

Office Action issued in Chinese Patent Application No. 201010613246.8 dated Mar. 30, 2012 (with translation).

Office Action issued in Chinese Patent Application No. 201010613246.8 dated Oct. 24, 2012 (with translation).

* cited by examiner

INTERMEDIATE COMPOUNDS OF TAMIFLU, METHODS OF PREPARATION AND USES THEREOF

FIELD OF INVENTION

The present invention relates to the intermediate compounds of Tamiflu, methods of preparation and uses thereof.

PRIOR ARTS

Tamiflu®, the scientific name Oseltamivir, the Chinese name Oseltamivir (trade name Tamiflu), is the ethyl ester prodrug of GS-4071. Tamiflu can block the pyrolysis of sialic acid residues on the surface of virus infected cell, which is caused by influenza virus NA, thus inhibit newly formed virus from releasing from the host cells. Oseltamivir has highly oral activity, after being metabolized by liver esterase in vivo, activated GS-4071 is produced, which arises the efficacy of inhibition of influenza virus NA.

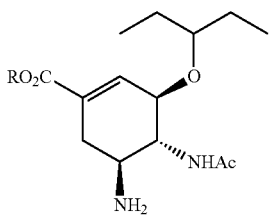

R = H, GS-4071, $IC_{50}$ = 1 nM;
R = $CH_2CH_3$, GS-4104, Tamiflu

Oseltamivir was studied and produced by Roche and sold in Switzerland in 1999. Oseltamivir tablet, the first conveniently oral influenza virus NA inhibitor, was for the treatment of type A and type B influenza, and also can reduce otitis media complication for 1~12-year-old patients. Tamiflu phosphate (Oseltamivir phosphate, GS-4101/002) was approved for sale for preventing type A and type B influenza on people over the age of 13 by FDA in 2000. In addition, Tamiflu possesses good tolerance and no serious side effects of Tamiflu have been reported.

There are several main preparation routes of Tamiflu:

At present, the most sophisticated preparation route used in industry was developed by Roche, in which shikimic acid ((−)-shikimic acid) was used as raw material (*J. Am. Chem. Soc.*, 1997, 119, 681).

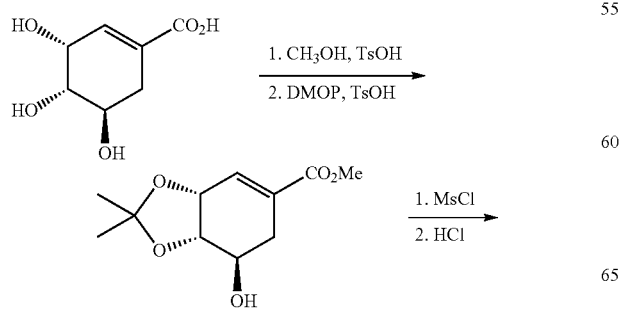

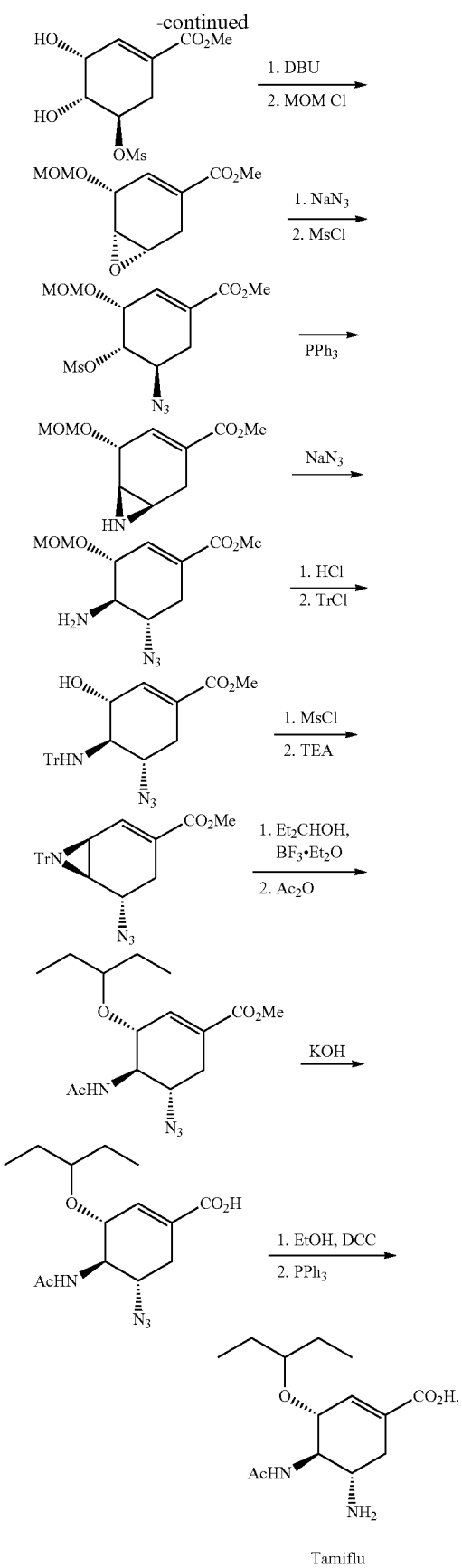

Tamiflu

The preparation route proposed by Corey in 2006 had 12 steps, and the overall yield was 27% (*J. Am. Chem. Soc.,* 2006, 128, 6310).
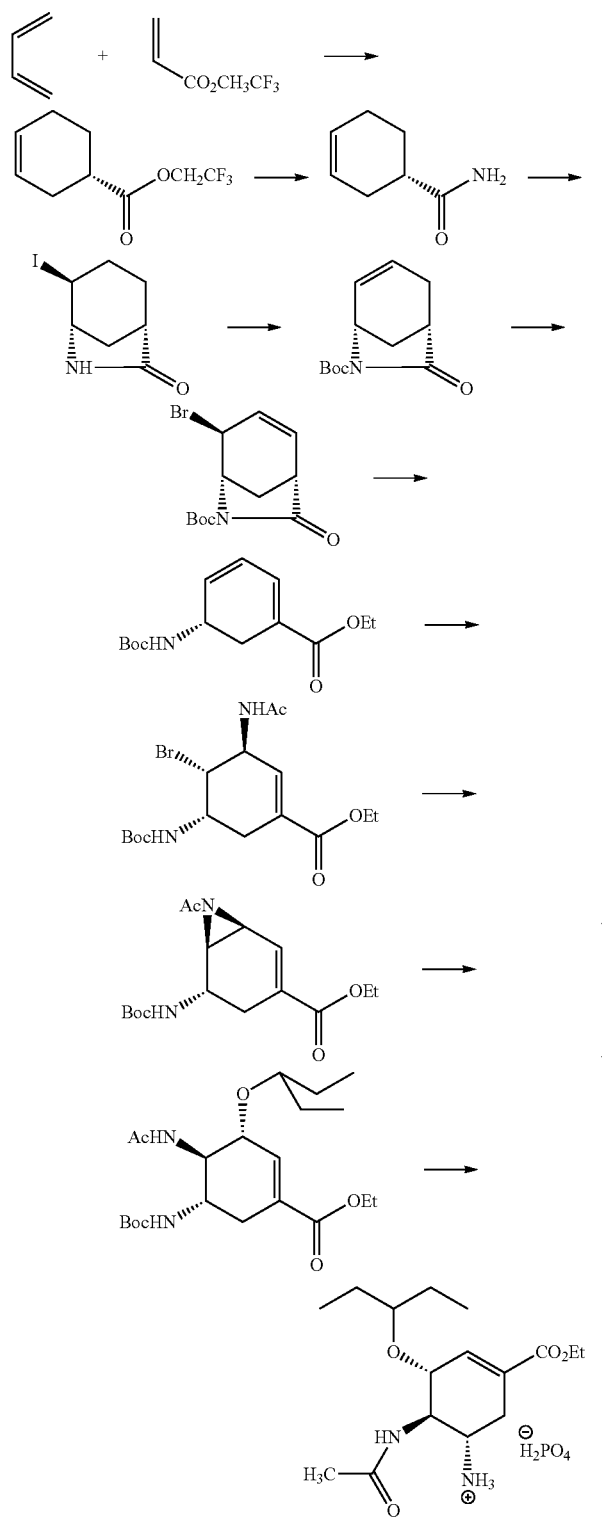
The preparation route proposed by Trost in 2008 had 8 steps, and the overall yield was 30% (*Angew. Chem. Int. Ed.* 2008, 47, 3759).
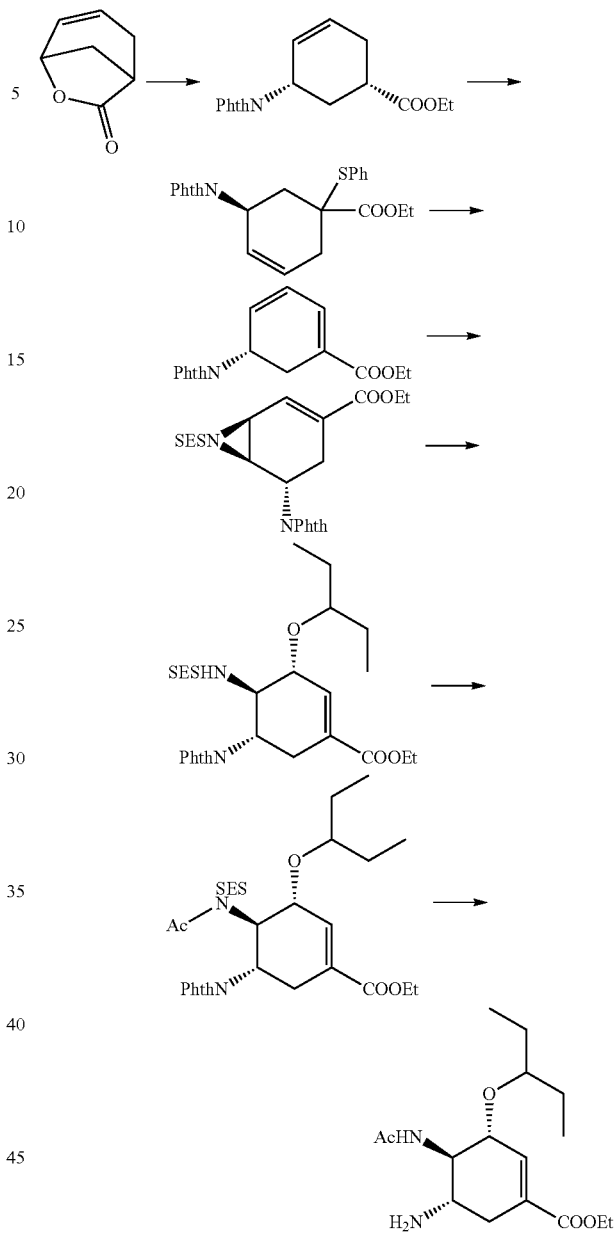
The overall yield of the preparation route proposed by Hayashi in 2009 was 57% (*Angew. Chem. Int. Ed.* 2009, 48, 1304).

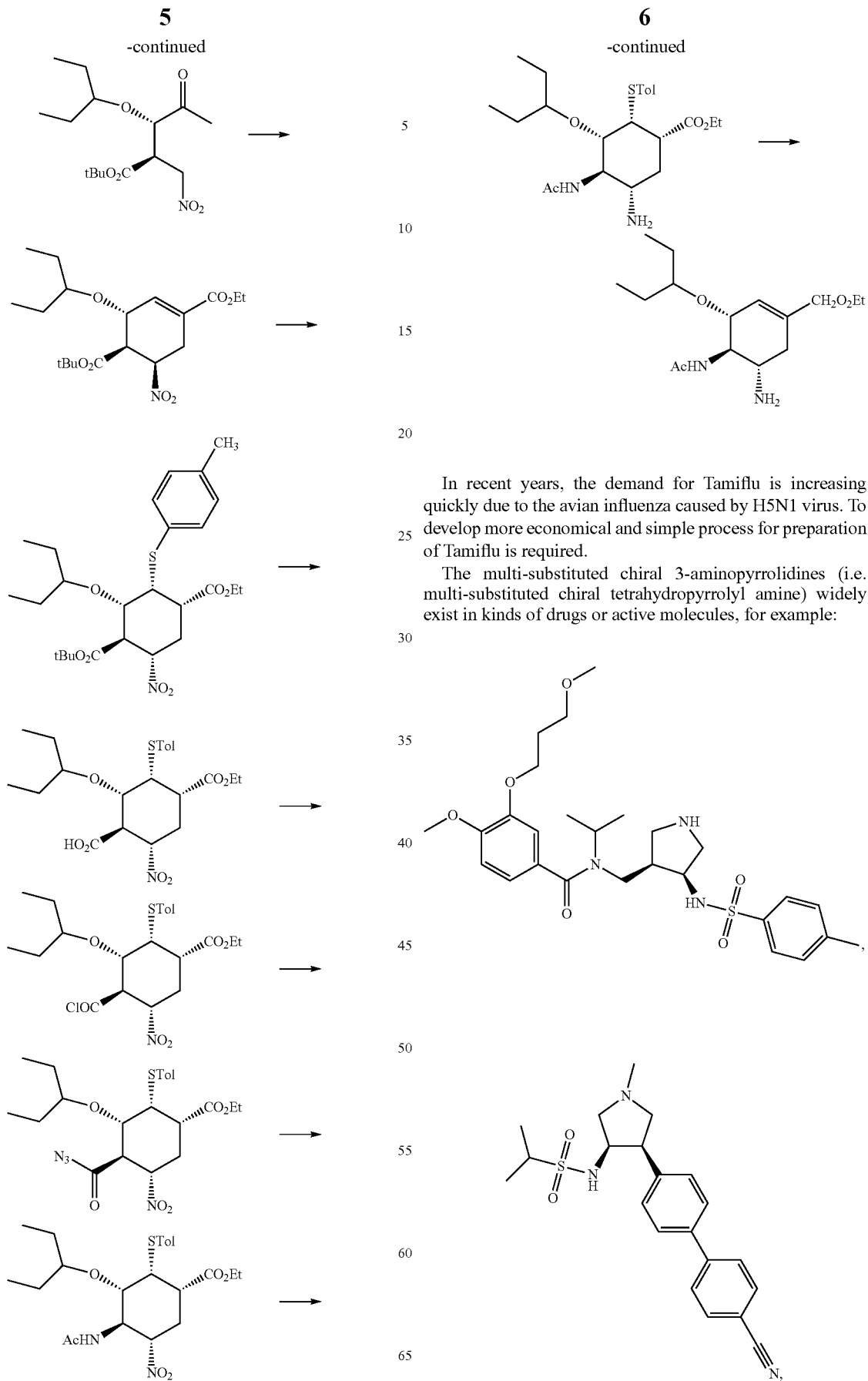

In recent years, the demand for Tamiflu is increasing quickly due to the avian influenza caused by H5N1 virus. To develop more economical and simple process for preparation of Tamiflu is required.

The multi-substituted chiral 3-aminopyrrolidines (i.e. multi-substituted chiral tetrahydropyrrolyl amine) widely exist in kinds of drugs or active molecules, for example:

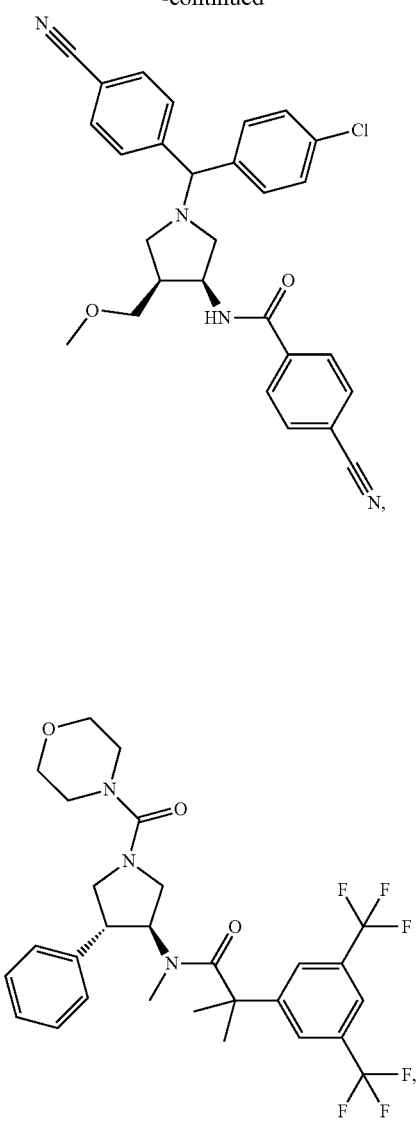

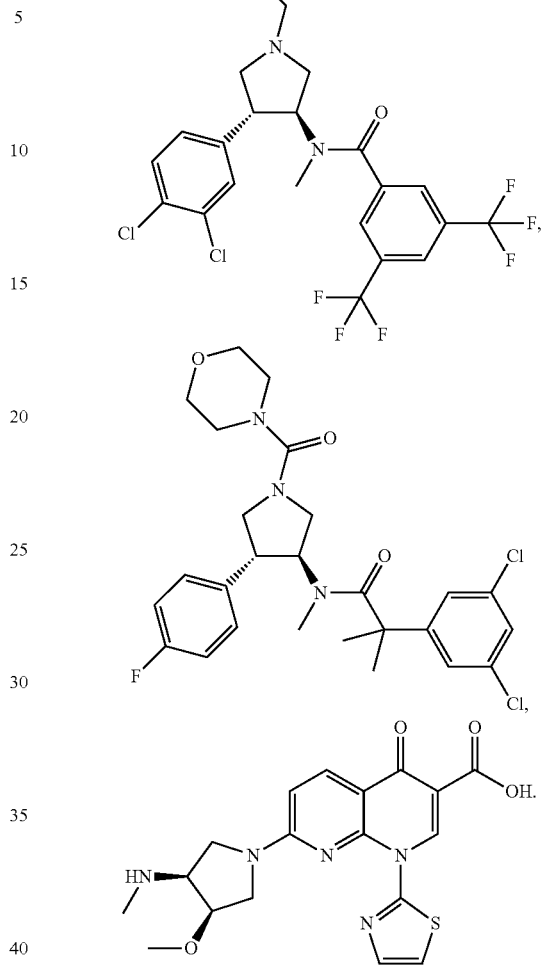

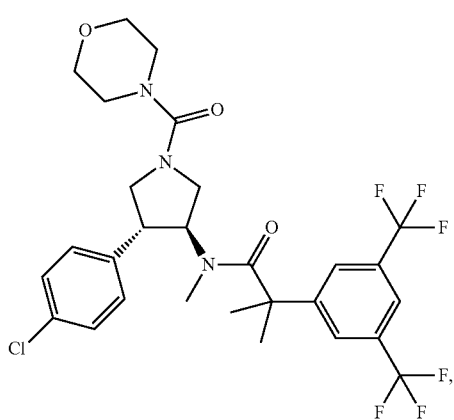

The present methods for preparing multi-substituted chiral 3-aminopyrrolidines have several defects, for example, long routes, low yields, poor selectivity, complex operation and high cost etc., therefore, to develop an economical and simply operated method for preparing multi-substituted chiral 3-aminopyrrolidines is urgently required.

Asymmetric catalysis provides a new powerful tool for preparing complex molecules efficiently. At the beginning of this century, organic catalysis (organocatalysis) developed quickly and became a new field in asymmetric catalysis by the efforts of Barbas, List and MacMillan et. al. (*Angew. Chem. Int. Ed* 2001, 40, 3726).

Organocatalysis is a bridge between organometallic catalysis and enzyme catalysis as well as synthetic chemistry and bioorganic chemistry. Due to the advantages of wide sources, easy preparation, and low price of catalysts, as well as their simple operation (usually anhydrous and oxygen-free operation are not required) and no residue of toxic metal, organocatalysis arouses great interest in chemical field and industrial field, and is continuously reviewed by authoritative academic journals and has become a hot topic at present.

Enantioselective Michael addition reaction using chiral catalysts has so far been considered as the most powerful and reliable method for the formation of C—C bond and C-heteroatom bond, and there are lots of examples in total synthesis. In recent years, lots of organocatalytic Michael reactions have been reported, including a variety of nucleophilic reagents and Michael receptors (*Synthesis* 2007, 14, 2065-2092). At the same time, it becomes a hot research field currently that applying Michael reaction to domino or one-pot process for the effective preparation of complex molecules with multi-chiral centers.

Recently, significant progress has been developed on the mechanism research about enamine or imminium transition state which formed by chiral amines and carbonyl compounds in organocatalysis. The most important target for chemists is to design such a catalyst which is suitable for most asymmetric reactions. To achieve this target usually requires great efforts in screening catalysts monotonously. However, only a few catalysts are excellent. For example, diarylprolinol ethers found by Jorgensen and Hayashi has got attention recently, and have been successfully applied to α-functionalization of aldehyde such as the formation of C—X bond (X=F, Br, S), α-amination, and Mannich reaction etc.

Enders disclosed an organic catalyzed tricomponent tandem reaction in Nature in 2006 (*Nature* 2006, 441, 861), in which a six-membered ring with four chiral centers and multi-functional groups is prepared via an one-pot Michael/Michael/Adol tandem process through active enamine, iminium and enamine intermediates.

stituted enantiopure 3-aminopyrrolidines used as medicament intermediates can be synthesized more easily and economically.

The other aim of present invention is to provide two kinds of intermediate compounds of Tamiflu.

The chiral amino compounds provided by the present invention have any one of the following structure:

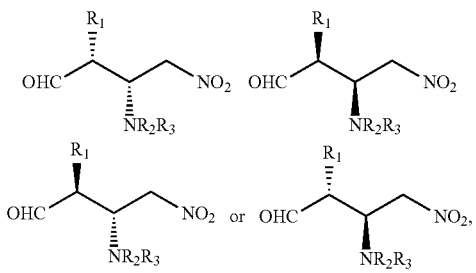

Wherein, $R_1$ is alkyl having 1~10 carbon atoms, alkoxy having 1~10 carbon atoms (preferably 3-pentyloxy), alkenyl having 2~6 carbon atoms (preferably isobutenyl), alkyl having 1~4 carbon atoms and substituted by $R_4$, aryl having 5~12 carbon atoms (preferably having 6 carbon), aryl having 5~12

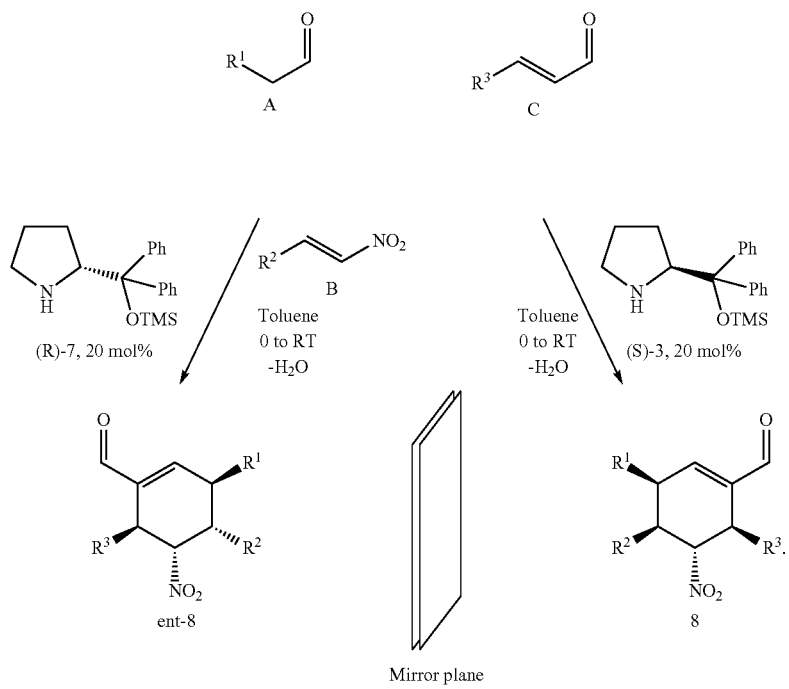

Mirror plane

CONTENT OF THE PRESENT INVENTION

The aim of the present invention is to provide a kind of chiral amine compounds, which can be used as key intermediates for assembling Tamiflu and some enantiopure 3-aminopyrrolidines that have potential usage for preparing clinically used drugs;

The other aim of the present invention is to further provide the preparation methods of said compounds, in which the raw materials are easily obtained, the operations are easy and suitable for industrial production.

The other aim of the present invention is to provide the uses of said compounds, which is to say, Tamiflu and multi-subcarbon atoms and monosubstituted or multisubstituted by electron-withdrawing group or electron-donating group. More preferably, $R_1$ is alkyl having 1~4 carbon atoms, alkoxy having 1~4 carbon atoms, alkyl having 1~4 carbon atoms substituted by $R_4$, phenyl, phenyl monosubstituted, disubstituted or trisubstituted by electron-withdrawing group or electron-donating group.

The $R_4$ is amino, substituted amino, hydroxyl, substituted hydroxyl (preferably benzyloxy), alkylacyloxy having 2~10 carbon atoms, or alkenyl having 2~6 carbon atoms; the substituents of said substituted amino is t-butoxycarbonyl, benzyloxycarbonyl, benzyl, acetyl, trifluoromethyl carbonyl or phthalyl

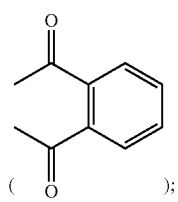

the substituents of said substituted hydroxyl is benzyl, acetyl, methoxymethyl, t-butyl dimethyl silyl, trimethylsilyl, triethylsilyl, t-butyl diphenyl silyl or 2-tetrahydropyranyl;

The said electron-withdrawing group is preferably halogen, cyano or nitro, the said halogen, for example, is F, Cl, Br or I, the said electron-donating group is preferably alkyl having 1~4 carbon atoms, alkoxy having 1~4 carbon atoms, amino or hydroxyl.

Wherein, $R_2$ and $R_3$ is independently selected from protecting group of nitrogen or hydrogen, the said protecting group of nitrogen is t-butoxycarbonyl, benzyloxycarbonyl, benzyl, acetyl, trifluoromethyl carbonyl, phthalyl

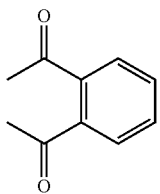

or other acyl protecting groups.

The chiral amino compounds in the present invention preferably have any one of the following structures or enantiomers thereof:

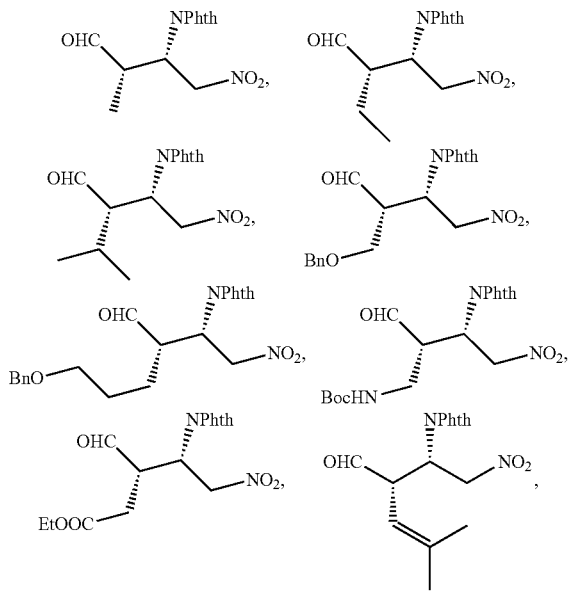

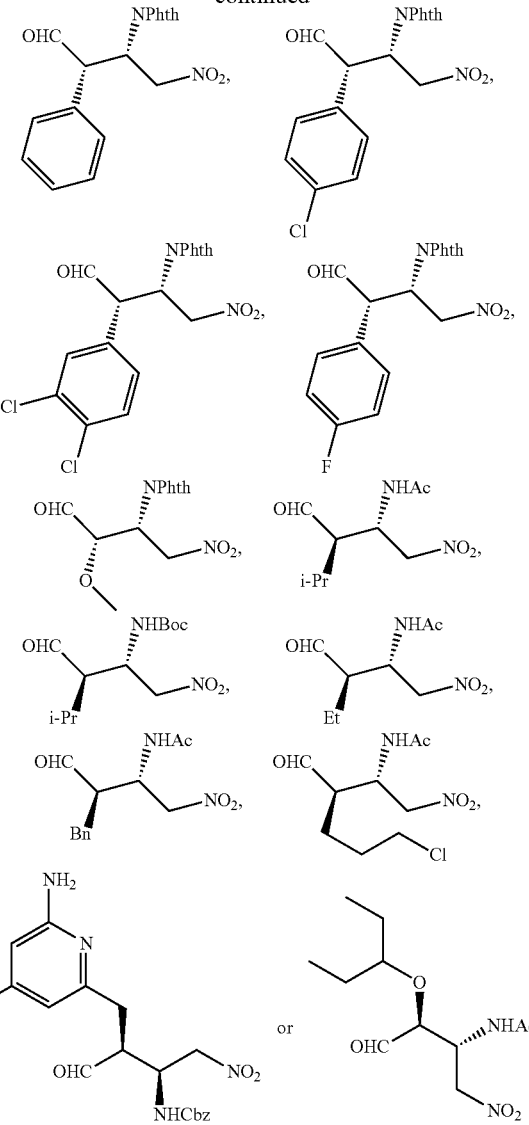

Wherein, Boc=t-butyloxycarbonyl; Bn=benzyl; Ac=acetyl; Phth=phthalyl; Cbz refers to benzyloxycarbonyl.

The general reaction equations for producing said chiral amino compounds

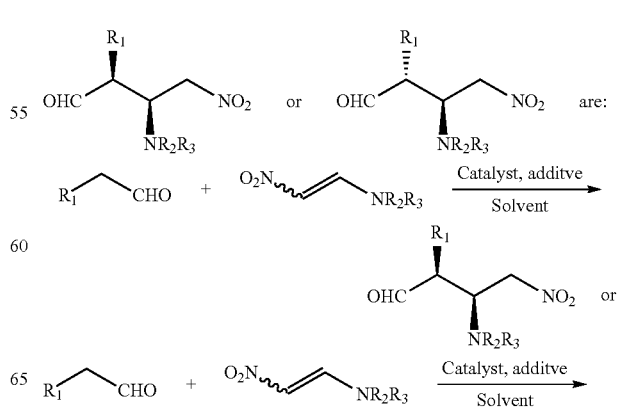

are:

-continued

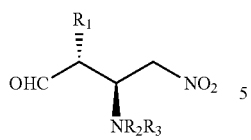

The general reaction equations for producing chiral amino compounds

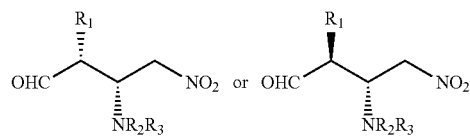

are almost the same as the above general reaction equations, except for that the catalyst is the corresponding enantiomers.

Wherein, $R_1$, $R_2$ and $R_3$ are according to the above.

The preparation method of said chiral amino compounds in the present invention can be further described as:

The said aldehyde and nitroolefin react for 10 min~48 h in a certain solvent at the temperature of −20~30° C., in the presence of catalyst and additive. The reaction is preferably under the temperature of −20~30° C., the additive is organic acid or weak alkali salt.

Wherein, the catalyst has the following structure:

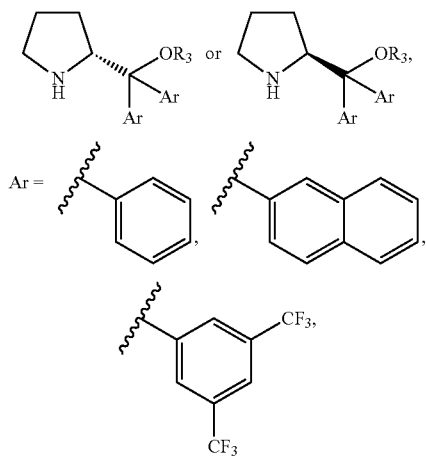

$R_3$ is according to above; for example, Di-t-butyl methyl silyl, trimethylsilyl, H or the combinations thereof; the additive is preferably one or more selected from organic acid or weak alkali salt consisting of acetic acid, sodium acetate, chloroacetic acid, bromoacetic acid, sodium acetate, benzoic acid and substituted benzoic acid; the solvent is preferably one or more selected from the group consisting of water, dichloromethane, 1,2-dichloroethane, acetonitrile, tetrahydrofuran, methanol, ethanol, toluene, N,N-dimethylformamide, dimethoxyethane and dimethyl sulfoxide;

The molar ratio of the aldehyde, nitroolefin, catalyst and additive is preferably (1.0-4.0):(1.0-2.0):(0.01-0.20):(0-0.50).

The chiral amino compound

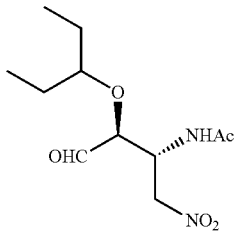 [SMILES: CCC(CC)O[C@H](C=O)[C@@H](C[N+](=O)[O-])NC(C)=O]

with high optical purity (dr=5:1, ee=96%) can be produced in a large scale (in the level of gram) through the preparation method in the present invention.

The present invention further relates to a preparation method of Tamiflu, which includes the following steps:
(1) Carrying out reduction reaction of nitro group of compound II to prepare compound I;
(2) Removing the $R_5SH$ from compound I;

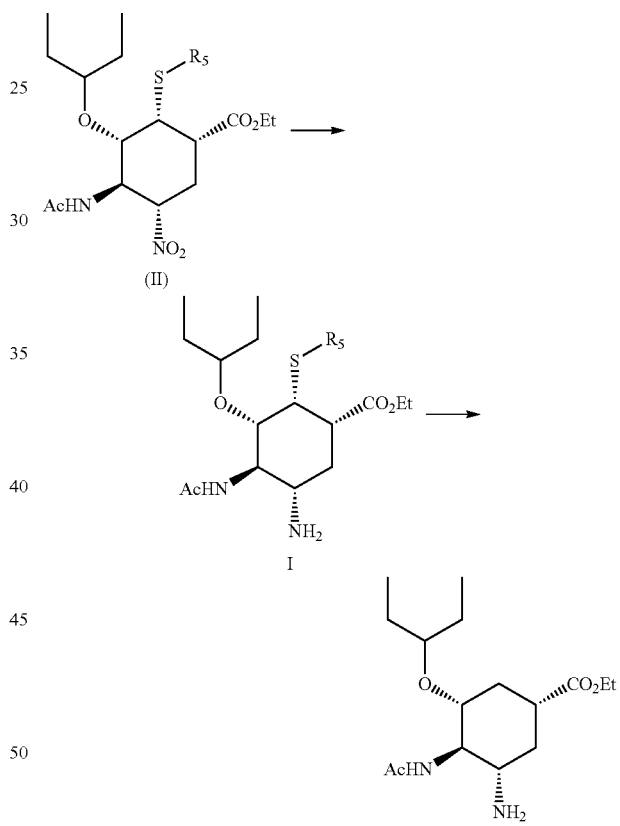

Wherein, $R_5$ refers to unsubstituted, monosubstituted or multi-substituted aryl having 6~12 carbon atoms or alkyl having 1~6 carbon atoms, the substituent group of aryl is halogen, nitro, alkyl having 1~3 carbon atoms or alkoxy having 1~3 carbon atoms, more preferably p-methylphenyl.

In step (1), the methods and conditions used for said reduction reaction can be commonly used for this kind of reactions in this field, the present invention particularly adopts the following methods and conditions: Compound I is prepared by the reduction reaction of nitro group of compound II in the presence of Zinc powder and trimethylchlorosilane, acetic acid or hydrochloric acid in solvent. Wherein, the solvent is preferably alcohol solvents, such as ethanol and/or methanol, more preferably ethanol. The volume mass ratio of the solvent to compound II is preferably 10~40 ml/g. The amount of zinc powder is preferably 10~30 times mole of compound II, more preferably 20 times mole of compound II. The amount of trimethylchlorosilane is preferably 10~20 times mole of compound II, more preferably 15 times mole of compound II. The volume mass ratio of acetic acid or hydrochloric acid to compound II is preferably 10~40 ml/g, more preferably 25 ml/g. The acetic acid or hydrochloric acid is preferably in the form of aqueous solution. The concentration of aqueous hydrochloric acid solution is preferably 0.1M~12M, the concentration of aqueous acetic acid solution is preferably 1%~100%. The reaction is preferably stopped until the reactant is consumed completely as monitored, generally the reaction time is 1-3 h. The temperature of the reaction is preferably 40~80° C., more preferably 70° C.

In step (2), the methods and conditions used for removing $R_5S$ can be commonly used for this kind of reactions in this field, the present invention particularly adopts the following methods and conditions: removing $R_5SH$ from compound I under the effect of alkali and ammonia gas in solvent. Wherein, the solvent is preferably alcohol solvents, such as ethanol and/or methanol, more preferably ethanol. The volume mass ratio of solvent to compound II is preferably 10~40 ml/g. The alkali is preferably potassium carbonate. The amount of alkali is preferably 5~15 times mole of compound II. The amount of ammonia is preferably 10~25 times mole of compound II. The reaction is preferably stopped until the reactant is consumed completely as monitored, generally the reaction time is 5-20 min. The reaction temperature is preferably −10~30° C., more preferably 0° C.

The compound II in the present invention can be prepared by the following method: Carrying out addition reaction of compound III as follows;

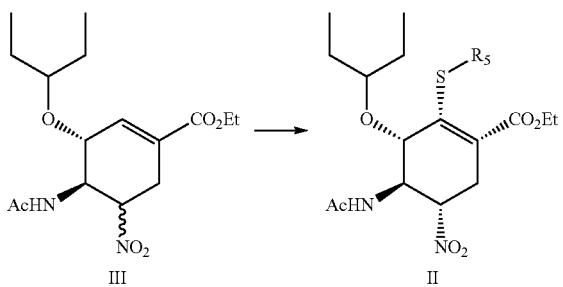

Wherein, $R_5$ is according to the above.

Wherein, the methods and conditions used for the addition reaction can be commonly used for this kind of reactions in this field, the present invention particularly adopts the following methods and conditions: carrying out addition reaction of compound III and $R_5SH$ in solvent. Wherein, the solvent is preferably alcohol solvent, such as ethanol and/or methanol, more preferably ethanol. The volume mass ratio of solvent to compound III is preferably 2~20 ml/g. The amount of the $R_5SH$ is preferably 2~10 times mole of compound III. The reaction is preferably stopped until the reactant is consumed completely as monitored, generally the reaction time is 1-3 days. The reaction temperature is preferably −20~30° C., more preferably −15° C.

The compound III in the present invention can be prepared by the following method: carrying out the reaction of compound IV and ethyl 2-diethoxyphosphinoylacrylate as follows;

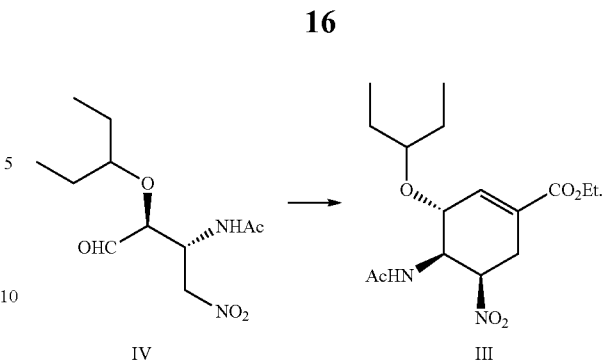

Wherein, the methods and conditions used for the reaction can be commonly used for this kind of reactions in this field, the present invention particularly adopts the following methods and conditions: carrying out reaction of compound IV and ethyl 2-diethoxyphosphinoylacrylate in the presence of base and solvent. Wherein, the solvent is preferably one or more selected from the group consisting of dichloromethane, chloroform, toluene, ethanol and methanol, more preferably dichloromethane and/or ethanol. The volume mass ratio of solvent to compound IV is preferably 2~20 ml/g. The alkali is preferably inorganic carbonate alkali or organic alkali. The organic alkali can be DBU etc. The alkali is preferably cesium carbonate. The amount of alkali is preferably 2~10 times mole of compound IV, more preferably 4 times. The reaction is preferably stopped until the reactant is consumed completely as monitored, generally the reaction time is 1-5 h. The reaction temperature is preferably −10~30° C., more preferably 30° C.

The present invention also relates to a preparation method of an intermediate compound I' of Tamiflu, which includes the following steps: carrying out the removal of ester group and elimination of hydroxy group of compound II';

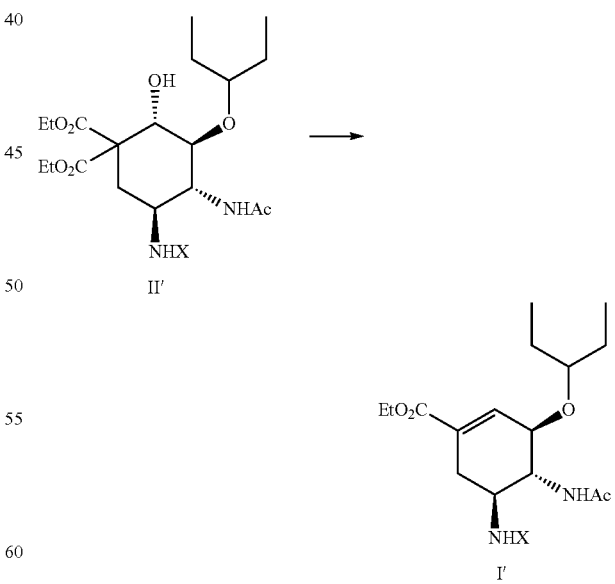

Wherein, X is the commonly used amino protecting group in this field, such as t-butoxycarbonyl (Boc);

Wherein, the methods and conditions used for the removal of ester group and elimination of hydroxy group can be commonly used for this kind of reactions in this field, the present invention particularly adopts the following methods and conditions: carrying out the removal of ester group and elimination of hydroxy group of compound II' in the presence of the inorganic salt and solvent under the protection of inert gas. Wherein, the solvent is preferably one or more selected from the group consisting of dimethylformamide, xylene and dimethylsulfoxide, more preferably dimethylsulfoxide. The volume mass ratio of solvent to compound II' is preferably 2~100 ml/g. The inorganic salt is preferably one or more selected from the group consisting of sodium chloride, potassium chloride and lithium chloride. The amount of the inorganic weak alkali is preferably 0.1-5 times mole of compound II'. The inert gas can be argon or nitrogen. The reaction temperature is preferably 100~250° C., more preferably 150~180° C. The reaction is preferably stopped until the reactant is consumed completely as monitored, generally the reaction time is 2~10 h.

The compound II' in the present invention can be prepared by the following method: carrying out amino protection reaction of compound III';

The compound III' in the present invention can be prepared by the following method: carrying out the reduction reaction of nitro group of compound IV';

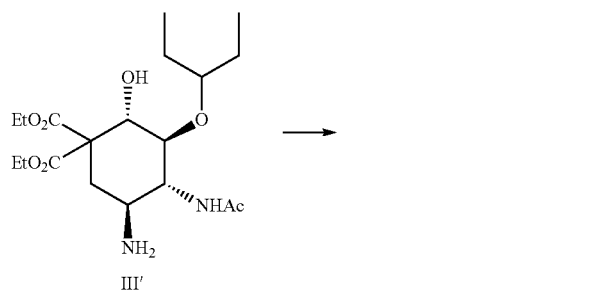

Wherein, the methods and conditions used for the reduction reaction of nitro group can be commonly used for this kind of reactions in this field, the present invention particularly adopts the following methods and conditions: carrying out reduction reaction of nitro group of compound IV' in the presence of Zn and acetic acid in solvent. Wherein, the solvent is preferably methanol and/or ethanol, more preferably ethanol. The volume mass ratio of the solvent to compound IV' is preferably 2~100 ml/g. The amount of the Zn is preferably 1~5 times mole of compound IV', more preferably 1.2~2 times mole of compound IV'. The amount of the acetic acid is preferably 1~5 times mole of compound IV', more preferably 1~2 times. The reaction temperature is preferably 0~60° C., more preferably 0~25° C. The reaction is preferably stopped until the reactant is consumed completely as monitored, generally the reaction time is 0.5~6 h.

The compound IV' in the present invention can be prepared by any of the following methods:

(1) Carry out isomerization reaction of compound V under the catalysis of alkali as follows;

Wherein, X can be the commonly used as amino protecting groups in this field, such as t-butoxycarbonyl (Boc).

Wherein, the methods and conditions used for amino protection reaction can be commonly used for this kind of reactions in this field, the present invention particularly adopts the following methods and conditions: when X is Boc, the reaction of compound III' and di-tert-butyl dicarbonate ester (Boc₂O) in solvent is carried out, providing N-t-butoxycarbonyl compound II'. Wherein, the solvent is preferably one or more selected from the group consisting of dichloromethane, tetrahydrofuran and acetonitrile, more preferably acetonitrile. The volume mass ratio of the solvent to compound III' is preferably 2~100 ml/g. The amount of di-tert-butyl dicarbonate ester is preferably 1~5 times mole of compound III', more preferably 1.0~1.5 times. The reaction temperature is preferably −20~50° C., more preferably 0~25° C. The reaction is preferably stopped until the reactant is consumed completely as monitored, generally the reaction time is 0.5~3 hours.

-continued

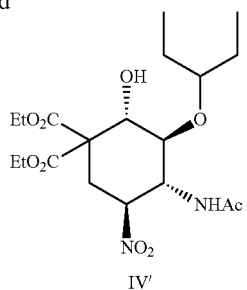

IV'

(2) Carry out intermolecular addition reaction and intramolecular aldol reaction of compounds IV and ethyl 2-ethoxy carbonyl acrylate under the catalysis of alkali;

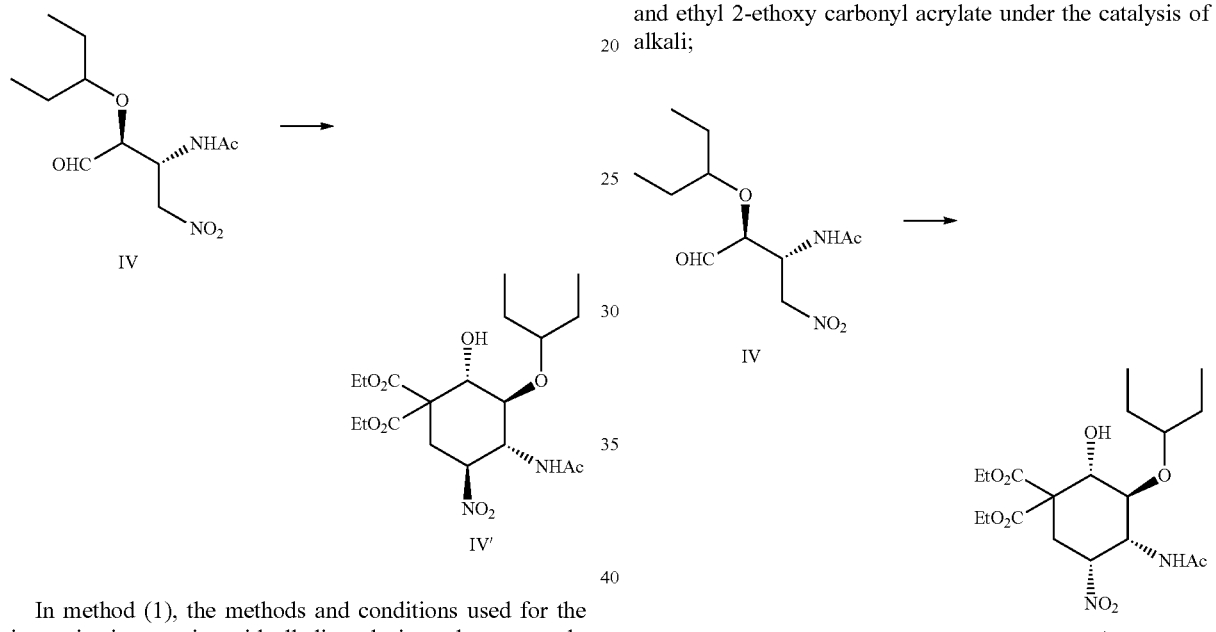

In method (1), the methods and conditions used for the isomerization reaction with alkali catalysis can be commonly used for this kind of reactions in this field, the present invention particularly adopts the following methods and conditions: carry out isomerization reaction of compound V' in the presence of inorganic weak alkali and solvent. Wherein, the solvent is preferably one or more selected from the group consisting of dichloromethane, tetrahydrofuran and acetonitrile, more preferably acetonitrile. The volume mass ratio of solvent to compound V' is preferably 2~100 ml/g. The inorganic weak alkali is preferably one or more selected from the group consisting of cesium carbonate, sodium carbonate, potassium phosphate and potassium carbonate, more preferably potassium carbonate. The amount of the inorganic weak alkali is preferably 0.1~5 times mole of compound V', more preferably 0.1~2 times. The reaction temperature is preferably −20~60° C., more preferably 0~25° C. The reaction is preferably stopped until the reactant is consumed completely as monitored, generally the reaction time is 1~48 h.

In method (2), the methods and conditions used for the reaction can be commonly used for this kind of reactions in this field, the present invention particularly adopts the following methods and conditions: carry out intermolecular addition reaction and intramolecular aldol reaction of compound IV and ethyl 2-ethoxy carbonyl acrylate in the presence of inorganic weak alkali and solvent. Wherein, the solvent is preferably one or more selected from the group consisting of dichloromethane, tetrahydrofuran and acetonitrile, more preferably acetonitrile. The inorganic weak alkali is preferably one or more selected from the group consisting of cesium carbonate, sodium carbonate, potassium phosphate and potassium carbonate, more preferably potassium carbonate. The amount of the inorganic weak alkali is preferably 0.1~5 times mole of compound IV, more preferably 0.1~2 times. The molar ratio of compound IV to ethyl 2-ethoxy carbonyl acrylate is preferably 0.1~1, more preferably 0.3~1. The reaction temperature is preferably −20~50° C., more preferably 0~25° C. The reaction is preferably stopped until the reactant is consumed completely as monitored, generally the reaction time is 1~10 h.

The compound V' in the present invention can be prepared by the following method: carry out intermolecular addition reaction and intramolecular aldol reaction of compounds IV and ethyl 2-ethoxy carbonyl acrylate under the catalysis of alkali;

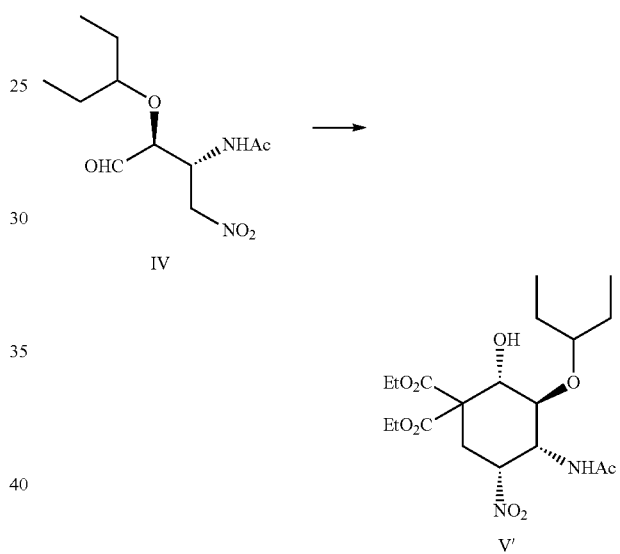

Wherein, the methods and conditions used for the reaction are the same as that in preparation method (2) of compound IV'. In the reaction, compound IV' and compound V' are simultaneously prepared, and can be purified respectively according to the common method in this field.

Therefore, Tamiflu can be prepared by the chiral amino compounds in the present invention, and the preparation method is more convenient and economical. The preferable preparation routes are shown as below:

The first preparation route:

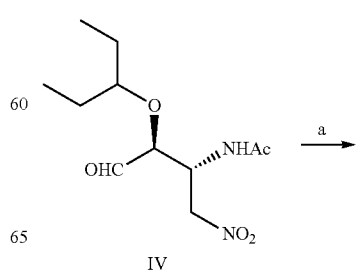

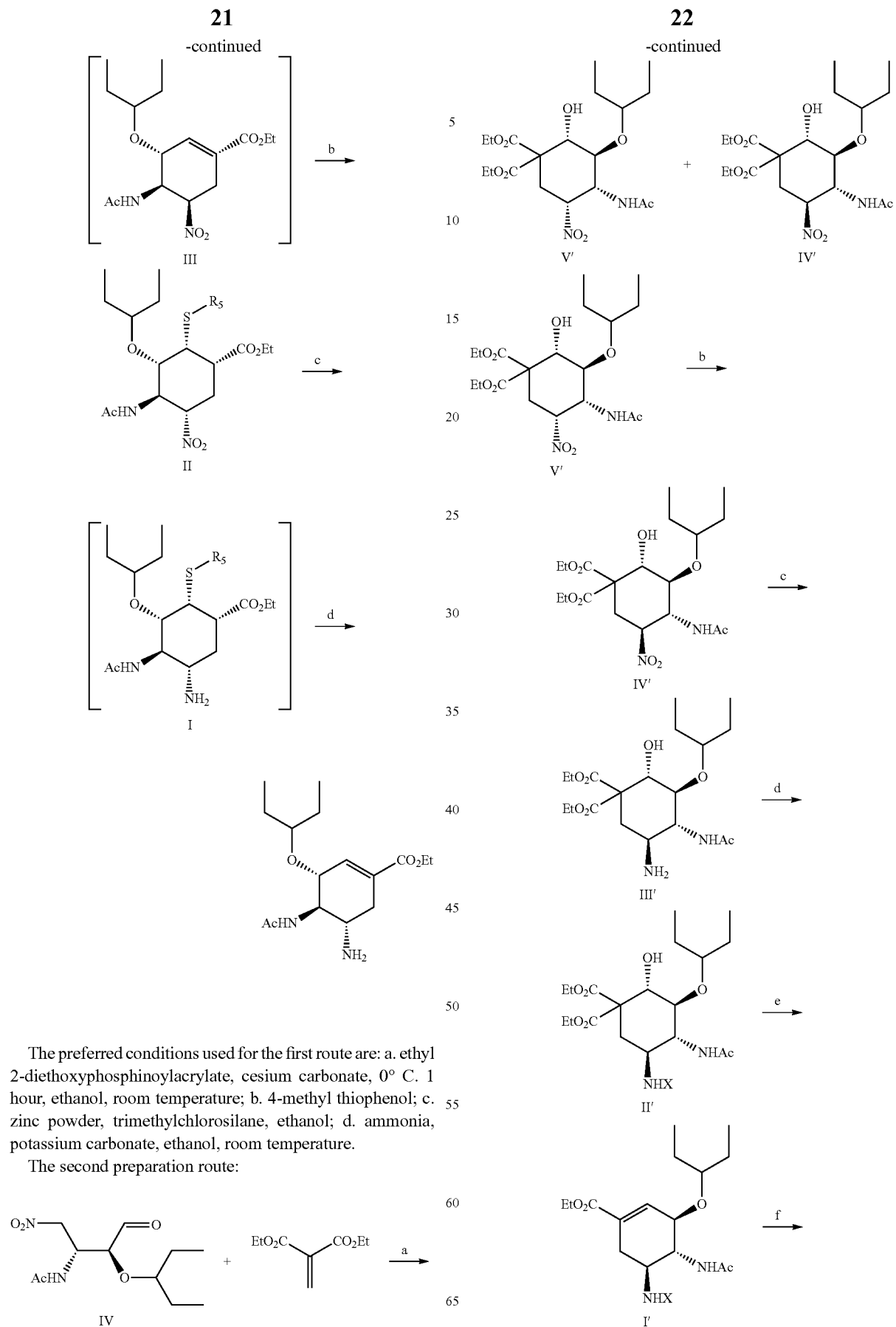
The preferred conditions used for the first route are: a. ethyl 2-diethoxyphosphinoylacrylate, cesium carbonate, 0° C. 1 hour, ethanol, room temperature; b. 4-methyl thiophenol; c. zinc powder, trimethylchlorosilane, ethanol; d. ammonia, potassium carbonate, ethanol, room temperature.
The second preparation route:

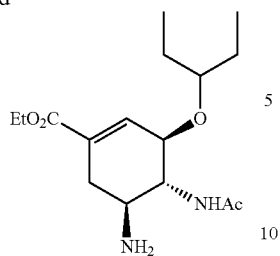

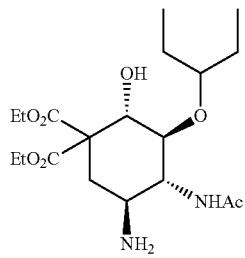

The preferred conditions used for the second route are: a. potassium carbonate, acetonitrile, 0° C., 3 h, and then room temperature, 6 h; b. potassium carbonate, acetonitrile, room temperature, 24 h; c. zinc powder, acetic acid, ethanol, 70° C.; d. X=Boc, (Boc)$_2$O, acetonitrile, room temperature; e. lithium chloride, dimethylsulfoxide, 190° C.; f. TFA, dichloromethane.

Wherein, X is according to the above.

The present invention further relates to an intermediate compound III, II, II', III', IV' or V' of Tamiflu:

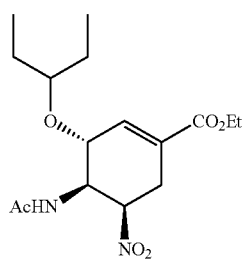

III

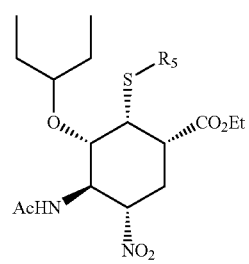

II

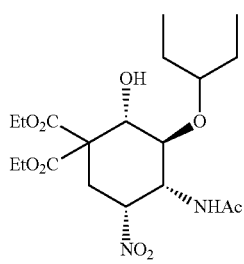

V'

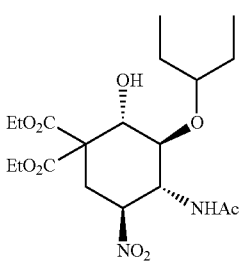

IV'

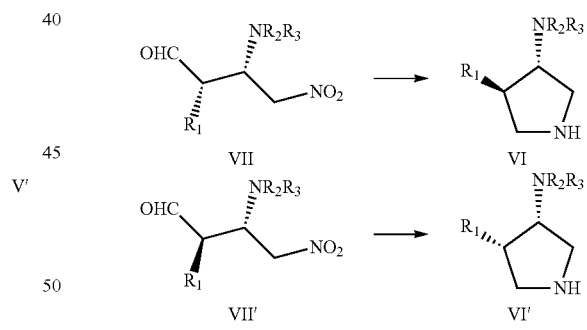

Wherein, X is the commonly used amino protecting group in this field, such as t-butoxycarbonyl (Boc). $R_5$ refers to unsubstituted, monosubstituted or multi-substituted aryl having 6~12 carbon atoms, or alkyl having 1~6 carbon atoms. The substituent of aryl is halogen, nitro, alkyl having 1~3 carbon atoms or alkoxy having 1~3 carbon atoms.

The chiral 3-aminopyrrolidines can also be prepared by the chiral amino compounds in the present invention. The intermediates are multi-substituted chiral 3-aminopyrrolidines, preferably disubstituted 3-aminopyrrolidines.

The present invention further relates to a preparation method of chiral 3-aminopyrrolidines shown as formula VI or formula VI', which includes the following steps: carrying out reduction reaction of nitro group and reductive amination reaction of compound VII or VII'.

Wherein, $R_1$, $R_2$ and $R_3$ are according to the above.

The preparation method is preferably any of the following methods:

The first method, carrying out reduction reaction of nitro group and reductive amination reaction of compound VII or VII' in the presence of catalyst, hydrogen gas, and polar solvent;

The second method, in solvent, carrying out reduction reaction of nitro group of compound VII or VII' firstly, and then carrying out reductive amination reaction.

In the two methods, the methods and conditions used for the reduction reaction of nitro group and reductive amination reaction can be commonly used for this kind of reactions in this field, the present invention particularly adopts the following methods and conditions:

In the first method, the polar solvent is preferably alcohol solvent, such as methanol and/or ethanol etc., more preferably methanol. The volume mass ratio of solvent to compound VII or VII' is preferably 50~200 ml/g. The catalyst is preferably Pd/C, Pd (OH)$_2$/C, PtO$_2$ or Ranny-Ni. The weight ratio of compound VII or VII' to the catalyst is preferably 1:0.001-0.2. The hydrogen pressure is preferably $1\times10^5$ Pa~$100\times10^5$ Pa. The reaction is preferably stopped until the two reactions are detected to react completely. The temperature of the two reactions are preferably 0° C.-100° C., more preferably 20° C.

In the second method, the reduction reaction of nitro group particularly adopts the following methods and conditions: carrying out reduction reaction of nitro group of compound VII or VII' in the presence of Zn/HOAc, Fe powder, or Ranny-Ni/H$_2$ in solvent. Wherein, the usage and the amount of Zn/HOAc, Fe powder, or Ranny-Ni/H$_2$ can be commonly used for this kind of reactions in this field. When the reducing agent is Zn/HOAc or Fe powder, the amount of the Zn (such as zinc powder) or Fe powder is preferably 10~30 times mole of compound VII or VII', more preferably 25 times. The solvent is preferably acetic acid or the mixture of acetic acid and water (volume ratio is preferably 1:0.5~2), the volume mass ratio of solvent to compound VII or VII' is preferably 20~100 ml/g. The reduction reaction is preferably stopped until the reactant is consumed completely as monitored, generally the reaction time is 1-24 h. The reaction temperature is preferably 0° C.~100° C., more preferably 20° C.

When the reducing agent is Ranny-Ni/H$_2$, the weight ratio of compound VII or VII' to the catalyst Ranny-Ni is preferably 1:0.001-0.2. The hydrogen pressure is preferably $1\times10^5$ Pa~$100\times10^5$ Pa. The most preferable solvent is alcohol solvent, such as ethanol and/or methanol, the reduction reaction is preferably stopped until the reactant is consumed completely as monitored, generally the reaction time is 1-24 h. The reaction temperature is preferably 0° C.-100° C., more preferably 20° C.

In the second method, the reductive amination reaction particularly adopts the following methods and conditions: carrying out reductive amination reaction of the substances prepared by the reduction reaction of nitro group under the effect of reducing agent in solvent. Wherein, the solvent is preferably one or more selected from the group consisting of dichloromethane, tetrahydrofuran and 1,2-dichloromethane. The volume mass ratio of solvent to compound VII or VII' is preferably 20~100 ml/g. The reducing agent is preferably sodium borohydride, sodium cyanoborohydride, acetic acid sodium borohydride, borane/pyridine, sodium borohydride/magnesium perchlorate, zinc borohydride/zinc chloride, or sodium triacetoxyborohydride. The amount of reducing agent is preferably 1~4 times mole of compound VII or VII'. The reaction is preferably stopped until the reactant is consumed completely as monitored, generally the reaction time is 0.5-2 h. The reaction temperature is preferably 0~30° C.

In the present invention, the mentioned optimal technical features can be optionally combined, based on the general knowledge in this field, to obtain preferred embodiments.

A variety of drug or bioactive molecule can be further prepared by the multi-substituted chiral 3-aminopyrrolidines. For example: orphan drug voreloxin

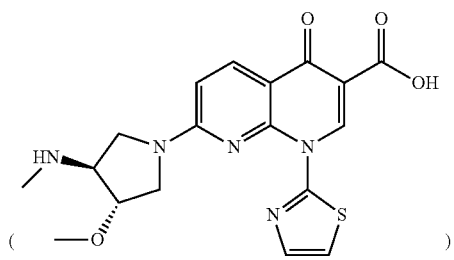 [SMILES: CN[C@H]1CN(c2ccc3c(=O)c(C(=O)O)cn(-c4nccs4)c3n2)C[C@@H]1OC]

for treating acute myeloid leukemia

The preparation method refers to *Drugs of the Future* 2009, 34, 363.

In the present invention, unless otherwise indicated, the materials or reagents can be commercially available.

In summary, the present invention provides a preparation method of chiral amino compounds, and a preparation method of Tamiflu by using this intermediates. In the methods, the raw materials are easy to be obtained, the operations are simple, the routes are short, and the methods are suitable for industrial production. The present invention also relates to a process for preparing the multi-substituted chiral 3-aminopyrrolidines by the intermediate compounds.

DETAILED DESCRIPTION OF THE PREFERRED EMBODIMENT

The following examples contributes to the understanding of the present invention, but the present invention is not limited thereto.

Embodiment 1

The preparation of

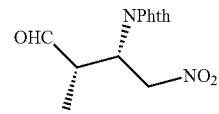

To a suspension of catalyst

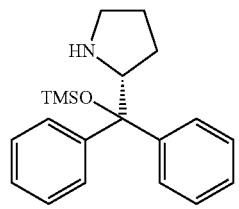

(5 mol %), nitroolefin (1 mmol) and acetic acid (5 equiv. of catalyst) in acetonitrile (2 mL) were added aldehyde (1.5 mmol) at 0° C. The reaction mixture was stirred until nitroolefin was consumed as monitored by TLC. The product was given after removing the solvent and the column chromatography (eluant: petroleum ether/ethyl acetate=5:1). Yield: 98%. The proportion of diastereoisomers is determined by H$^1$ NMR of crude product, dr: 11:1, the optical purity is determined by chiral HPLC column, ee: 98%. NMR analysis: $^1$H NMR (400 MHz, CDCl$_3$) δ 9.72 (s, 1H), 7.87-7.85 (m, 2H), 7.78-7.76 (m, 2H), 5.24 (dt, 1H, J=3.2, 10.4 Hz), 5.17 (dd, 1H, J=2.8, 12.8 Hz), 4.85 (dd, 1H, 2.8, 12.8 Hz), 3.37-3.29 (m, 1H), 1.15 (d, 3H, J=7.6 Hz); $^{13}$C NMR (100 MHz, CDCl$_3$) δ 200.54, 167.74, 134.73, 131.12, 123.85, 73.68, 48.36, 45.84, 11.09; mass spectrometry: HRMS calcd for C$_{13}$H$_{13}$N$_2$O$_5$ (M+H)$^+$ m/z 277.0819. found 277.0821; specific rotation: [α]$_D^{22}$=−104.8 (c=1.00 in CHCl$_3$).

Embodiment 2

The preparation of

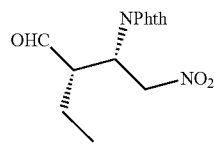

To a suspension of catalyst

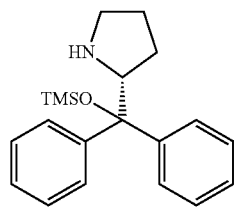

(5 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 98%. The proportion of diastereoisomers is determined by H$^1$ NMR of crude product, dr: 15:1, the optical purity is determined by chiral HPLC column, ee: 99%. NMR analysis: $^1$H NMR (400 MHz, CDCl$_3$) δ 9.76 (d, 1H, J=0.8 Hz), 7.89-7.87 (m, 2H), 7.81-7.76 (m, 2H), 5.32 (dt, 1H, J=3.6, 10.8 Hz), 5.13 (dd, 1H, J=10.4, 13.2 Hz), 4.82 (dd, 1H, J=3.2, 12.8 Hz), 3.41-3.36 (m, 1H), 1.87-1.80 (m, 1H), 1.64-1.57 (m, 1H), 0.90 (t, 3H, J=7.6 Hz); $^{13}$C NMR (100 MHz, CDCl$_3$) δ 201.28, 167.77, 134.81, 131.25, 123.98, 74.01, 51.49, 46.83, 19.54, 9.95; mass spectrometry: ESI-MS m/z 291.1 (M+H)$^+$, HRMS calcd for C$_{15}$H$_{18}$N$_2$NaO$_6$ (M+Na+MeOH)$^+$ m/z 345.1057. found 345.1071; specific rotation: [α]$_D^{22}$=−73.2 (c=1.13 in CHCl$_3$).

Embodiment 3

The preparation of

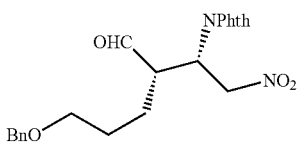

To a suspension of catalyst

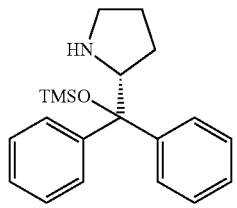

(5 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 98%. The proportion of diastereoisomers is determined by H$^1$ NMR of crude product, dr: 9:1, the optical purity is determined by chiral HPLC column, ee: 99%. NMR analysis: $^1$H NMR (400 MHz, CDCl$_3$) δ 9.74 (s, 1H), 7.84-7.82 (m, 2H), 7.74-7.72 (m, 2H), 7.34-7.26 (m, 1H), 7.25-7.22 (m, 2H), 7.16-7.14 (m, 2H), 5.31 (dt, 1H, J=3.2, 10.4 Hz), 5.14 (dd, 1H, J=10.4, 12.8 Hz), 4.78 (dd, 1H, J=3.2, 13.2 Hz), 4.32 (s, 2H), 3.42-3.38 (m, 1H), 3.35 (t, 2H, J=5.6 Hz), 1.88-1.80 (m, 1H), 1.74-1.61 (m, 1H), 1.52-1.43 (m, 2H); $^{13}$C NMR (100 MHz, CDCl$_3$) δ 201.02, 167.70, 138.17, 134.65, 131.16, 128.34, 127.53, 127.44, 123.84, 73.85, 72.70, 68.90, 50.34, 47.09, 25.61, 23.16; mass spectrometry: ESI-MS m/z 465.2 (M+Na+MeOH)$^+$, HRMS calcd for C$_{23}$H$_{26}$N$_2$NaO$_7$ (M+Na+MeOH)$^+$ m/z 465.1632. found 465.1637; specific rotation: [α]$_D^{22}$=−45.89 (c=1.26 in CHCl$_3$).

Embodiment 4

The preparation of

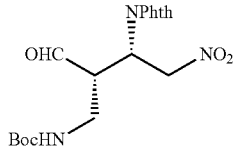

To a suspension of catalyst

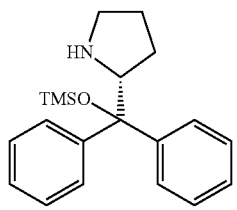

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 99%. The proportion of diastereoisomers is determined by H$^1$ NMR of crude product, dr: 8:1, the optical purity is determined by chiral HPLC column, ee: >99%. NMR analysis: $^1$H NMR (400 MHz, CDCl$_3$) δ 9.83 (s, 1H), 7.88-7.85 (m, 2H), 7.80-7.78 (m, 2H), 5.43-5.34 (m, 1H), 5.23 (dd, 1H, J=10.4, 13.6 Hz), 4.93 (dd, 1H, J=-3.2, 13.6 Hz), 4.85 (t, 1H, J=11.2 Hz), 3.96-3.89 (m, 1H), 3.49-3.41 (m, 1H), 3.16-3.10 (m, 1H), 1.40 (s, 9H); mass spectrometry: MS (m/z) 391.3 (M$^+$); specific rotation: $[\alpha]_D^{22}=-75.4$ (c=1.00 in CHCl$_3$).

Embodiment 5

The preparation of

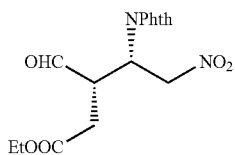

To a suspension of catalyst

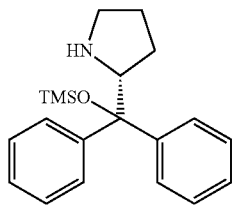

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 98%. The proportion of diastereoisomers is determined by H$^1$ NMR of crude product, dr: 7:1, the optical purity is determined by chiral HPLC column, ee: 96%. NMR analysis: $^1$H NMR (400 MHz, CDCl$_3$) δ 9.84 (s, 1H), 7.89-7.86 (m, 2H), 7.79-7.77 (m, 2H), 5.41-5.36 (m, 2H), 4.97 (dd, 1H, J=3.2, 13.2 Hz), 4.04 (q, 2H, J=7.2 Hz), 3.58-3.52 (m, 1H), 2.71-2.68 (m, 2H), 1.18-1.14 (t, 3H, J=14.7 Hz); mass spectrometry: MS (m/z) 348.3 (M$^+$); specific rotation: $[\alpha]_D^{22}=-43.1$ (c=1.00 in CHCl$_3$).

Embodiment 6

The preparation of

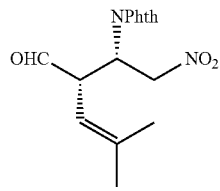

To a suspension of catalyst

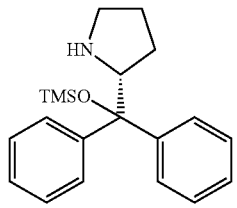

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 97%. The proportion of diastereoisomers is determined by H$^1$ NMR of crude product, dr: 11:1, the value of ee is determined by chiral HPLC column, ee: 98%. NMR analysis: NMR (400 MHz, CDCl$_3$) δ 9.67 (S, 1H,), 8.03-8.01 (m, 2H), 7.94-7.92 (m, 2H), 5.56 (dt, 1H, J=3.6, 10.8 Hz), 5.38 (dd, 1H, J=10.8, 13.2 Hz), 5.01 (dd, 1H, J=3.2, 13.2 Hz), 4.91 (d, 1H, J=10.0 Hz), 4.44 (q, 1H, J=10.4 Hz), 1.82 (d, 3H, J=27.2 Hz); $^{13}$C NMR (100 MHz, CDCl$_3$) δ 196.52, 167.81, 144.15, 134.61, 131.31, 123.78, 113.15, 73.65, 52.25, 47.47, 26.07, 18.74; mass spectrometry: ESI-MS m/z 317.1 (M+H)$^+$, HRMS calcd for C$_{17}$H$_{20}$N$_2$NaO$_6$ (M+MeOH+Na)$^+$ m/z 371.1213. found 371.1220; specific rotation: $[\alpha]_D^{22}=-231.5$ (c=1.00 in CHCl$_3$)

Embodiment 7

The preparation of

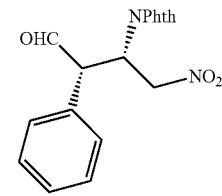

To a suspension of catalyst

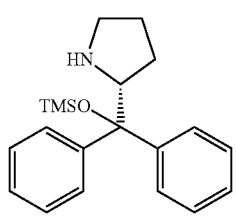

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 99%. The proportion of diastereoisomers is determined by H$^1$ NMR of crude product, dr: 12:1, the value of ee is determined by chiral HPLC column, ee: 98%.

NMR analysis: ¹H NMR (400 MHz, CDCl₃) δ 9.70 (s, 1H), 7.70-7.63 (m, 4H), 7.24-7.14 (m, 5H), 5.71 (dt, 1H, J=3.2, 10.8 Hz), 5.25 (dd, 1H, J=10.8, 13.2 Hz), 4.95 (dd, 1H, J=3.2, 12.8 Hz), 4.60 (d, 1H, J=11.6 Hz); ¹³C NMR (100 MHz, CDCl₃) δ 196.73, 167.43, 134.41, 130.92, 130.14, 129.61, 129.52, 129.10, 123.54, 74.13, 57.91, 48.17; mass spectrometry: ESI-MS m/z 393.1 (M+Na+MeOH)⁺, HRMS calcd for $C_{18}H_{14}N_2NaO_5$ (M+Na)⁺ m/z 361.0795. found 361.0810; specific rotation: $[\alpha]_D^{22}$=−276.48 (c=1.00 in CHCl₃).

Embodiment 8

The preparation of

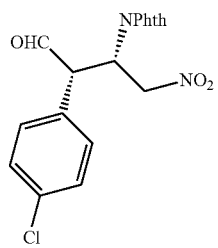

To a suspension of catalyst

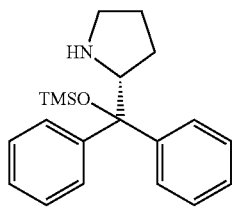

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was disappeared completely by TLC detection. The product was given after removing the solvent and the column chromatography (eluant: petroleum ether/ethyl acetate=5:1). Yield: 99%. The proportion of diastereoisomers is determined by H¹ NMR of crude product, dr: 14:1, the value of ee is determined by chiral HPLC column, ee: 95%. NMR analysis: NMR (400 MHz, CDCl₃) δ 9.66 (s, 1H), 7.72-7.66 (m, 4H), 7.23 (d, 2H, J=8.4 Hz), 7.11 (d, 2H, J2.1 Hz), 5.68 (dt, 1H, J=3.2, 10.8 Hz), 5.22 (dd, 1H, J=10.4, 13.2 Hz), 4.93 (dd, 1H, J=3.2, 13.6 Hz), 4.62 (d, 1H, J=11.2 Hz); ¹³C NMR (100 MHz, CDCl₃) δ 196.24, 167.42, 135.28, 134.61, 130.90, 130.82, 129.83, 128.71, 123.72, 74.03, 57.23, 47.92; mass spectrometry: ESI-MS m/z 373.0 (M+H)⁺, HRMS calcd for $C_{18}H_{13}ClN_2NaO_5$ (M+Na)⁺ m/z 395.0405. found 395.0409; specific rotation: $[\alpha]_D^{22}$=−221.1 (c=1.00 in CHCl₃).

Embodiment 9

The preparation of

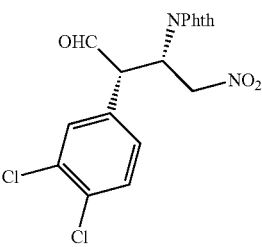

To a suspension of catalyst

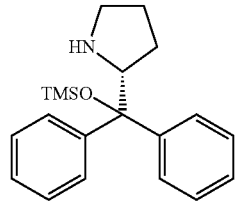

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 98%. The proportion of diastereoisomers is determined by H¹ NMR of crude product, dr: 15:1, the value of ee is determined by chiral HPLC column, ee: 96%. NMR analysis: NMR (400 MHz, CDCl₃) δ 9.65 (s, 1H), 7.75-7.73 (m, 2H), 7.02-7.66 (m, 2H), 7.35 (d, 1H, J=8 Hz), 7.30 (d, 1H, J=2 Hz), 7.02 (dd, 1H, J=2, 8 Hz), 5.67 (dt, 1H, J=3.6, 10.8 Hz), 5.20 (dd, 1H, J=10.4, 12.8 Hz), 4.90 (dd, 1H, J=3.2, 13.2 Hz); ¹³C NMR (100 MHz, CDCl₃) δ 195.64, 167.44, 134.79, 133.93, 133.81, 131.67, 131.64, 130.84, 130.41, 128.51, 123.93, 73.93, 57.03, 47.79; mass spectrometry: ESI-MS m/z 407.4 (M+H)⁺, HRMS calcd for $C_{19}H_{16}Cl_2N_2NaO_6$ (M+MeOH+Na)+m/z 461.0277. found 461.0291; specific rotation: $[\alpha]_D^{22}$=−153.9 (c=1.00 in CHCl₃).

Embodiment 10

The preparation of

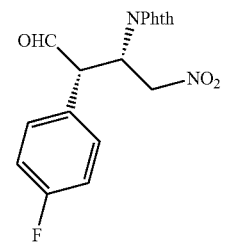

To a suspension of catalyst

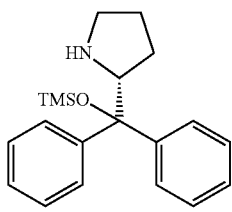

(10 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 99%. The proportion of diastereoisomers is determined by $H^1$ NMR of crude product, dr: 15:1, the value of ee is determined by chiral HPLC column, ee: 95%. NMR analysis: $^1$H NMR (400 MHz, CDCl$_3$) δ 9.68 (s, 1H), 7.71-7.64 (m, 4H), 7.15 (dd, 2H, J=5.2, 8.8 Hz), 6.94 (t, 2H, J=8.4 Hz), 5.67 (dt, 1H, J=3.2, 10.8 Hz), 5.23 (dd, 1H, J=10.8, 13.2 Hz), 4.60 (d, 1H, J=11.2 Hz); $^{13}$C NMR (100 MHz, CDCl$_3$) δ 196.46, 167.43, 162.91 (d, J=248 Hz), 134.56, 131.41 (d, J=8.1 Hz), 130.83, 126.02 (d, J=4.0 Hz), 123.64, 116.65 (d, J=22.3 Hz), 74.05, 57.06, 48.07; $^{19}$F NMR (300 MHz, CDCl$_3$) δ −112.14; mass spectrometry: ESI-MS m/z 357.1 (M+H)$^+$, HRMS calcd for C$_{19}$H$_{17}$FN$_2$NaO$_6$ (M+MeOH+Na)$^+$ m/z 411.0963. found 411.0977; specific rotation: $[\alpha]_D^{22}$=−241.8 (c=1.00 in CHCl$_3$).

Embodiment 11

The preparation of

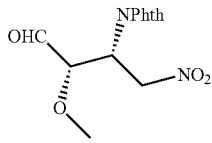

To a suspension of catalyst

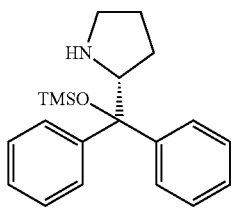

(5 mol %), nitroolefin (1 mmol) and acetic acid (5 equiv. of catalyst) in acetonitrile (2 mL) were added aldehyde (1.5 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=5:1). Yield: 95%. The proportion of diastereoisomers is determined by $H^1$ NMR of crude product, dr: 5:1, the value of ee is determined by chiral HPLC column, ee: 95%. NMR analysis: $^1$H NMR (400 MHz, CDCl$_3$) δ 9.68 (s, 1H), 7.71-7.64 (m, 4H), 7.15 (dd, 2H, J=5.2, 8.8 Hz), 6.94 (t, 2H, J=8.4 Hz), 5.67 (dt, 1H, J=3.2, 10.8 Hz), 5.23 (dd, 1H, J=10.8, 13.2 Hz), 4.60 (d, 1H, J=11.2 Hz); mass spectrometry: MS (m/z) 292.1 (M$^+$); specific rotation: $[\alpha]_D^{22}$=−95.2 (c=1.00 in CHCl$_3$).

Embodiment 12

The preparation of

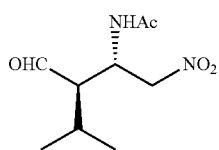

To a suspension of catalyst

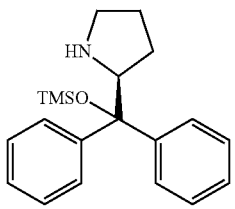

(10 mol %), nitroolefin (1 mmol) and acetic acid (1 equiv. of catalyst) in chloroform (2 mL) were added aldehyde (2 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=1:1). Yield: 98%. The proportion of diastereoisomers is determined by $H^1$ NMR of crude product, dr: 5:1, the value of ee is determined by chiral HPLC column, ee: 98%. NMR analysis: $^1$H NMR (400 MHz, CDCl$_3$) δ 9.82 (s, 1H), 6.55 (s, 1H), 5.01-4.95 (m, 1H), 4.59 (dd, J=6.4, 12.4 Hz, 1H), 4.47 (dd, 12.4 Hz, 1H), 2.60-2.57 (m, 1H), 2.14 (q, J=6.8 Hz, 1H), 1.99 (s, 3H), 1.16 (d, J=6.4 Hz, 3H), 1.09 (d, J=6.8 Hz, 3H). $^{13}$C NMR (100 MHz, CDCl$_3$) δ 205.43, 170.06, 77.00, 57.34, 45.89, 28.60, 23.31, 21.21, 20.00; mass spectrometry: ESI-MS m/z 217.0 (M+H)$^+$, HRMS (MALDI) calcd for C$_9$H$_{16}$N$_2$O$_4$Na (M+Na)$^+$ m/z 239.1002. found 239.1011; specific rotation: $[\alpha]_D^{22}$=+136.06 (c=2.0 in CHCl$_3$).

Embodiment 13

The preparation of

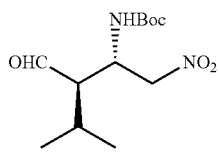 [SMILES: CC(C)[C@@H](C=O)[C@@H](C[N+](=O)[O-])NC(=O)OC(C)(C)C]

To a suspension of catalyst

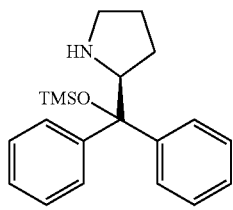

(10 mol %), nitroolefin (1 mmol) and acetic acid (1 equiv. of catalyst) in chloroform (2 mL) were added aldehyde (2 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=1:1). Yield: 93%. The proportion of diastereoisomers is determined by $H^1$ NMR of crude product, dr: 5:1, the value of ee is determined by chiral HPLC column, ee: 97%. NMR analysis: $^1$H NMR (400 MHz, CDCl$_3$): δ=9.81 (s, 1H), 5.40 (d, J=8.8 Hz, 1H), 4.68-4.64 (m, 1H), 4.62-4.55 (m, 1H), 4.52-4.44 (m, 1H), 2.52 (t, J=5.2 Hz, 1H), 2.22-2.15 (m, 1H), 1.43 (s, 9H), 1.16 (d, J=6.4 Hz, 3H), 1.10 (d, J=6.8 Hz, 3H). $^{13}$C NMR (100 MHz, CDCl$_3$): δ=205.01, 155.05, 80.58, 77.36, 57.63, 47.86, 28.32, 21.09, 20.01; mass spectrometry: ESI-MS: [M+Na]$^+$ 297.1, [M+MeOH+Na]$^+$ 329.3; HRMS (ESI) m/z calcd for $C_{12}H_{22}N_2O_5Na$ [M+Na]$^+$ 297.1427, found 297.1421; specific rotation: $[\alpha]_D^{22}$=+114.98 (c=1 in CHCl$_3$).

Embodiment 14

The preparation of

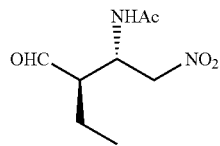

To a suspension of catalyst

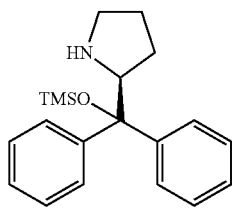

(10 mol %), nitroolefin (1 mmol) and acetic acid (1 equiv. of catalyst) in chloroform (2 mL) were added aldehyde (2 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=1:1). Yield: 95%. The proportion of diastereoisomers is determined by $H^1$ NMR of crude product, dr: 5:1, the value of ee is determined by chiral HPLC, ee: 98%. NMR analysis: $^1$H NMR (400 MHz, CDCl$_3$) δ 9.63 (s, 1H), 6.54 (s, 1H), 4.94-4.88 (m, 1H), 4.69 (dd, J=7.2, 12.8 Hz, 1H), 4.56 (dd, J=5.6, 12.4 Hz, 1H), 2.66 (q, J=5.6 Hz, 1H), 2.00 (s, 3H), 1.84 (quintet, J=6.8 Hz, 1H), 1.59 (quintet, J=7.2 Hz, 1H), 1.10 (t, J=7.6 Hz, 3H); $^{13}$C NMR (100 MHz, CDCl$_3$) δ 203.32, 170.46, 76.62, 53.84, 46.32, 23.11, 19.85, 11.81; mass spectrometry: ESI-MS m/z 203.1 (M+H)$^+$, HRMS (MALDI) calcd for $C_8H_{15}N_2O_4$ (M+H)$^+$ m/z 203.1026. found 203.1024; specific rotation: $[\alpha]_D^{22}$=+118.1 (c=1.01 in CHCl$_3$).

Embodiment 15

The preparation of

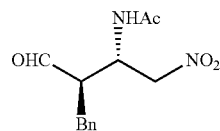 [SMILES: CC(=O)N[C@H](C[N+](=O)[O-])[C@H](C=O)Cc1ccccc1]

To a suspension of catalyst

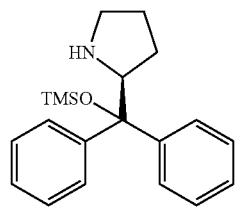

(10 mol %), nitroolefin (1 mmol) and acetic acid (1 equiv. of catalyst) in chloroform (2 mL) were added aldehyde (2 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=1:1). Yield: 93%. The proportion of diastereoisomers is determined by $H^1$ NMR of crude product, dr: 5:1, the value of ee is determined by chiral HPLC, ee: 98%. NMR analysis: $^1$H NMR (400 MHz, CDCl$_3$) δ 9.65 (s, 1H), 7.35-7.32 (m, 2H), 7.28-7.24 (m, 1H), 7.23-7.19 (m, 2H), 6.44 (s, 1H), 4.87-4.83 (m, 1H), 4.63 (dd, J=6.8, 12.4 Hz, 1H), 4.50 (dd, J=6.0, 12.4 Hz, 1H), 3.07 (m, 1H), 3.02 (dd, J=7.6, 13.6 Hz,), 2.88 (dd, J=6.4, 12.8 Hz, 1H), 2.00 (s, 3H); $^{13}$C NMR (100 MHz, CDCl$_3$) δ 203.07, 170.56, 136.76, 129.12, 128.98, 127.35, 76.61, 53.81, 47.10, 33.16, 23.15; mass spectrometry: ESI-MS m/z 265.1 (M+H)$^+$, HRMS calcd for $C_{13}H_{17}N_2O_4$ (M+H)$^+$ m/z 265.1182. found 265.1183; specific rotation: $[\alpha]_D^{22}$=+81.0 (c=1.1 in CHCl$_3$).

Embodiment 16

The preparation of

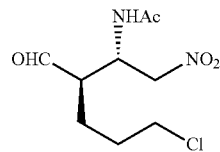 [SMILES: CC(=O)N[C@H](C[N+](=O)[O-])[C@H](C=O)CCCCl]

To a suspension of catalyst

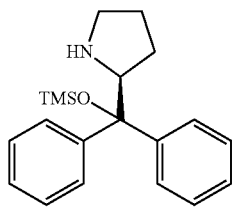

(10 mol %), nitroolefin (1 mmol) and acetic acid (1 equiv. of catalyst) in chloroform (2 mL) were added aldehyde (2 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=1:1). Yield: 80%. The proportion of diastereoisomers is determined by $H^1$ NMR of crude product, dr: 5:1, the value of ee is determined by chiral HPLC, ee: 98%. NMR analysis: $^1$H NMR (400 MHz, CDCl$_3$) δ 9.63 (s, 1H), 6.39 (d, J=8.8 Hz, 1H), 4.95-4.88 (m, 1H), 4.70 (dd, J=7.2, 13.2 Hz, 1H), 4.55 (dd, J=6.0, 12.8 Hz, 1H), 3.66-3.54 (m, 2H), 2.78-2.74 (m, 1H), 2.03-1.98 (m, 1H), 2.01 (s, 3H), 1.93-1.79 (m, 2H), 1.66-1.58 (m, 1H). $^{13}$C NMR (100 MHz, CDCl$_3$) δ 202.60, 170.63, 76.52, 51.72, 46.32, 44.33, 29.65, 23.40, 23.11; mass spectrometry: ESI-MS m/z 251.0 (M+H)$^+$, HRMS calcd for C$_{10}$H$_{19}$ClN$_2$NaO$_5$ (M+Na+MeOH)$^+$ m/z 305.0875. found 305.0835; specific rotation: $[\alpha]_D^{22}$=+111.7 (c=1.2 in CHCl$_3$).

Embodiment 17

The preparation of

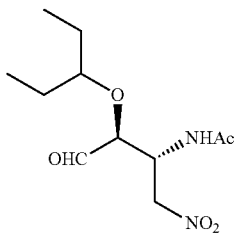 [SMILES: CCC(CC)O[C@H](C=O)[C@@H](C[N+](=O)[O-])NC(C)=O]

To a suspension of catalyst

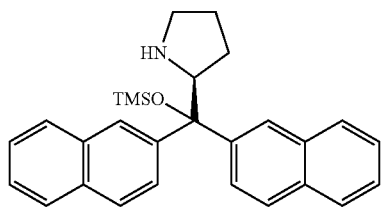

(10 mol %), nitroolefin (1 mmol) and benzoic acid (3 equiv. of catalyst) in chloroform (2 mL) were added aldehyde (2 mmol) at 0° C. After 1 hour the temperature was naturally raised to room temperature and the reaction mixture was stirred until nitroolefin was consumed as monitored by TLC. The product was given after removing the solvent and the column chromatography (eluant: petroleum ether/ethyl acetate=1:1). Yield: 81%. The proportion of diastereoisomers is determined by $H^1$ NMR of crude product, dr: 5:1, the value of ee is determined by chiral HPLC, ee: 96%. NMR analysis: $^1$H NMR (400 MHz, CDCl$_3$) δ 9.73 (s, 1H), 6.20 (d, 1H, J=8.4 Hz), 5.09-5.02 (m, 1H), 4.58 (d, 2H, J=6.8 Hz), 4.08 (d, 1H, J=3.2 Hz), 3.42-3.37 (m, 1H), 1.98 (s, 3H), 1.61-1.35 (m, 4H), 0.95-0.83 (m, 6H); $^{13}$C NMR (100 MHz, CDCl$_3$): δ=201.10, 170.30, 83.44, 79.75, 74.28, 48.21, 25.92, 24.96, 22.82, 9.28, 9.18; mass spectrometry: ESI-MS: [M+H]$^+$ 261.0; HRMS (ESI) m/z calcd for C$_{11}$H$_{20}$N$_2$NaO$_5$ [M+Na]$^+$ 283.1264, found 283.1264; specific rotation: $[\alpha]_D^{22}$=−2.2 (c=1.00 in CHCl$_3$).

Embodiment 18

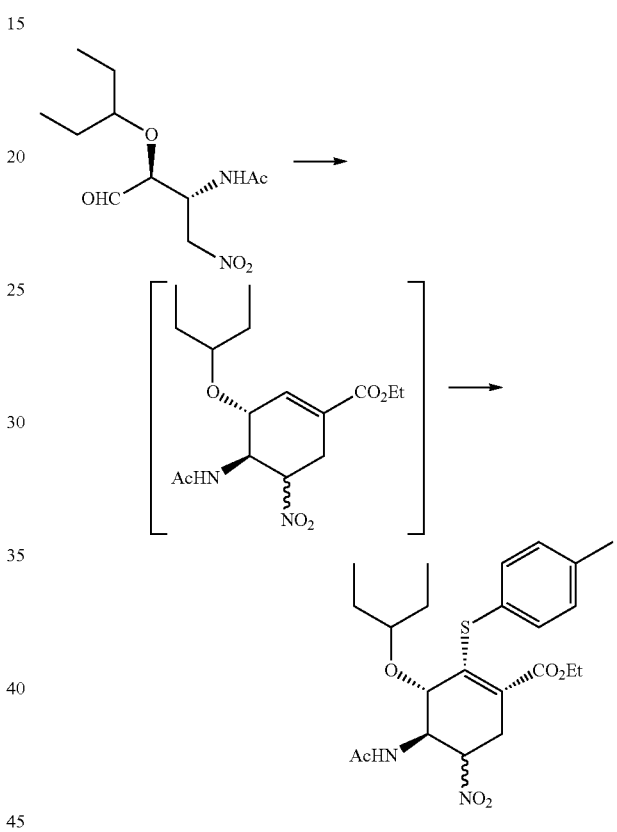

The reactant (1 mmol) was dissolved in dichloromethane, ethyl 2-diethoxyphosphinoylacrylate (1 mmol) and cesium carbonate (3 mmol) were added at room temperature. After 1 hour, the solvent was removed by vacuum evaporation. Then 3 ml of ethanol and 4-methyl thiophenol (4 mmol) were added at −15° C. The reaction mixture was stirred for 12 h and quenched by 1N aqueous hydrochloric acid, then extracted by chloroform for three times. The organic phase was washed by brine, dried by anhydrous magnesium sulfate. The solvent was removed by vacuum evaporation. The product was given by column chromatography (eluant: petroleum ether/ethyl acetate=2:1). Yield: 70%. The proportion of diastereoisomers is determined by $H^1$ NMR of crude product, the optical purity is determined by chiral HPLC column, ee: 96.40%. NMR analysis of intermediate: major isomer: $^1$H NMR (400 MHz, CDCl$_3$) δ 6.77 (m, 1H), 6.10 (d, J=6.8 Hz, 1H), 5.45-5.52 (ddd, J=6.0, 10.8, 16.8 Hz), 4.71-4.73 (m, 1H), 4.14-4.19 (q, J=7.2 Hz), 3.71-3.77 (m, 1H), 3.28 (quintet, J=5.6 Hz, 1H), 3.02 (td, J=6.4, 17.2 Hz), 2.77-2.85 (m, 1H), 1.90 (s, 1H), 1.39-1.49 (m, 4H), 1.23 (t, J=7.2 Hz, 3H), 0.84 (t, J=7.2 Hz, 1H), 0.82 (t, J=7.6 Hz, 1H); $^{13}$C (100 MHz, CDCl$_3$) δ170.2, 164.2, 137.0, 125.8, 81.2, 81.0, 70.9, 60.3, 55.0, 28.5, 25.2, 24.5, 22.4, 13.1, 8.5, 8.2. mass spectrometry: MS (m/z) 342.2 (M+); specific rotation: $[\alpha]_D^{22}$=−34 (c=1.00 in CHCl$_3$). minor isomer: $^1$H NMR (400 MHz, CDCl$_3$) δ 6.80 (t, J=2.0 Hz, 1H), 5.81 (d, J=8.4 Hz, 1H), 4.92 (ddd, J=3.2, 6.8, 8.6 Hz, 1H), 4.72 (m, 1H), 4.18 (q, J=7.2 Hz, 2H), 4.05 (m, 1H), 3.45 (q, J=5.6 Hz, 1H), 2.97 (d, J=7.2 Hz, 1H), 1.92 (s, 1H), 1.43-1.55 (m, 4H), 1.25 (t, J=7.2 Hz, 3H), 0.89 (t, J=7.2 Hz, 3H), 0.82 (t, J=8.0 Hz, 3H); mass spectrometry: MS (m/z) 342.2 (M+); specific rotation: $[\alpha]_D^{22}$=−65 (c=1.00 in CHCl$_3$). NMR analysis of product: $^1$H NMR (400 MHz, CDCl$_3$) δ 7.38 (d, 2H, J=8 Hz), 7.07 (d, 2H, J=8 Hz), 5.88 (d, 1H, J=6 Hz), 5.56-5.48 (m, 1H), 4.44 (dd, 1H, J=3.6, 10.4 Hz), 4.13-4.09 (m, 1H), 4.07-4.06 (m, 1H), 3.95-3.84 (m, 2H), 3.21-3.16 (m, 1H), 2.88 (dt, 1H, J=13.2, 3.2 Hz), 2.57-2.53 (m, 1H), 2.37 (q, 1H, J=13.2 Hz), 2.31 (s, 3H), 1.94 (s, 3H), 1.50-1.41 (m, 1H), 1.39-1.33 (m, 1H) 1.18 (t, 3H, J=7.2 Hz), 1.13-1.07 (m, 2H), 0.81 (t, 3H, J=7.2 Hz), 0.61 (t, 3H, J=7.6 Hz); $^{13}$C NMR (100 MHz, CDCl$_3$): δ=171.60, 170.19, 137.57, 132.84, 131.63, 129.63, 82.90, 80.92, 73.56, 61.55, 55.79, 54.26, 43.15, 28.06, 25.32, 24.22, 23.90, 21.16, 14.13, 9.25, 8.84; mass spectrometry: ESI-MS: [M+H]$^+$ 467.3, [M+Na]$^+$ 489.3; HRMS (ESI) m/z calcd for C$_{23}$H$_{34}$N$_2$NaO$_6$S [M+Na]$^+$ 489.2030, found 489.2031; specific rotation: $[\alpha]_D^{22}$=−47.65 (c=0.62 in CHCl$_3$).

added under the protection of argon at room temperature. The reaction mixture was stirred for 4 h at 70° C. and then was cooled to −20° C. After NH$_3$ gas was bubbled for 5 min at −20° C., the reaction temperature was raised to room temperature and then potassium carbonate (20 mmol) was added. And the reaction mixture was stirred for 6 h. The solvent was removed by vacuum evaporation, and 1N hydrochloric acid solution was added to dissolve. The solution was washed by ethyl acetate, and the pH value was adjusted to 12 by ammonia, extracted by chloroform for three times. The organic phase was washed by brine, dried by anhydrous magnesium sulfate, and after removing the solvent the product was given by vacuum evaporation. Yield: 92%. NMR analysis: NMR (400 MHz, CDCl$_3$) δ 6.78 (t, J=2.0 Hz, 1H), 5.62 (d, J=7.6 Hz, 1H), 4.20 (q, J=7.2 Hz, 2H), 4.15-4.20 (m, 1H), 3.52 (q, J=8.0 Hz, 1H), 3.34 (quintet, J=5.6 Hz, 1H), 3.24 (dt, J=5.2, 10.0 Hz, 1H), 2.75 (dd, J=17.6, 5.2 Hz, 1H), 2.15 (ddt, J=17.6, 10.0, 2.8 Hz, 1H), 2.04 (s, 3H), 1.40-1.60 (m, 4H), 1.29 (t, J=7.2 Hz, 3H), 0.90 (t, J=7.2 Hz, 3H), 0.89 (t, J=7.2 Hz, 3H); mass spectrometry: MS (m/z) 312.4 (M$^+$); specific rotation: $[\alpha]_D^{22}$=−54.9 (c 1.40, CHCl$_3$).

Embodiment 20

Embodiment 19

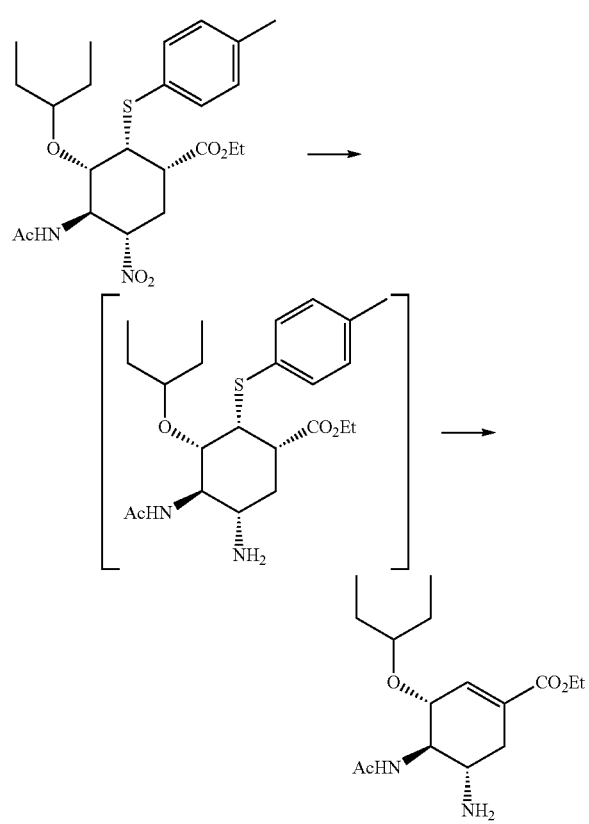

The reactant (1 mmol) was dissolved in ethanol, zinc powder (50 mmol) and trimethylchlorosilane (30 mmol) were The reactants (0.20 mmol) was dissolved in H$_2$O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 by 4M aqueous NaOH solution after filtering. The solution was extracted by CH$_2$Cl$_2$ (3*10 mL), washed by brine, dried by Na$_2$SO$_4$, and the product was given after removing the solvent by vacuum evaporation. Yield: 99%. The purity is greater than 95% in $^1$H NMR. The product with higher purity can be obtained through column chromatography. Eluent (AcOEt/(MeOH/NH$_3$)=12:1-8:1). NMR analysis: $^1$H NMR (400 MHz, CDCl$_3$): δ=7.77-7.75 (m, 1H), 7.58-7.53 (m, 2H), 7.50-7.45 (m, 1H), 6.09 & 5.95 (s, 1H), 5.00 (br, 2H), 4.66 & 4.30 (d, J=4.8 & 5.2 Hz, 1H), 3.58-3.53 (m, 0.5H), 3.44-3.37 (m, 1H), 3.09-3.05 (m, 1H), 3.03-2.99 (m, 0.5H), 2.51-2.36 (m, 2H); $^{13}$C NMR (100 MHz, CDCl$_3$): δ 167.35 & 167.13, 143.83 & 143.74, 132.21 & 132.16, 131.98 & 131.63, 129.47 &129.40, 123.28 & 123.13, 123.11 & 122.99, 81.41 & 80.11, 59.13 &57.95, 53.75 & 53.42, 51.54 & 48.85, 41.09 & 36.77, 19.67 & 19.04; mass spectrometry: ESI-MS: [M+H]$^+$ 233.0; HRMS (ESI) m/z calcd for C₁₃H₁₇N₂O₂ [M+H]⁺ 233.1284, found 247.1294; specific rotation: $[\alpha]_D^{24}$=−4.76 (c=1.33 in CHCl₃)

Embodiment 21

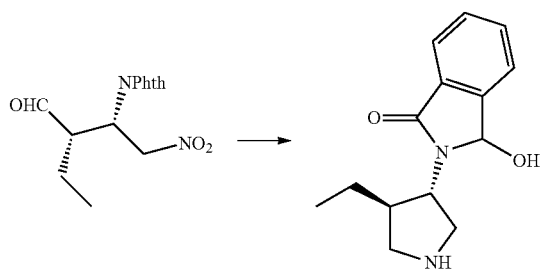

The reactants (0.20 mmol) was dissolved in H₂O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 with 4M aqueous NaOH solution after filtering. The solution was extracting by CH₂Cl₂ (3*10 mL), washed by brine, dried by anhydrous Na₂SO₄, and the product was given after removing the solvent. Yield: 99%. The purity is showed greater than 95% by ¹H NMR. The product with higher purity can be obtained by column chromatography. Eluent (AcOEt/(MeOH/NH₃)=12:1-8:1). NMR analysis: ¹H NMR (400 MHz, CDCl₃) δ 7.74-7.70 (m, 1H), 7.55-7.54 (m, 2H), 7.47-7.46 (m, 1H), 5.99 & 5.94 (s, 1H), 5.54 (br s, 2H), 4.66 & 4.24 (s, 1H), 3.48-3.43 & 3.31-3.30 (m, 1H), 3.31-3.30 & 3.05-3.02 (m, 1H), 2.92-2.86 (m, 1H), 2.47-2.42 & 2.31-2.29 (m, 1H), 2.31-2.29 & 2.22-2.18 (m, 1H), 1.72-1.66 & 1.57-1.52 (m, 1H), 1.46-1.40 & 1.39-1.31 (m, 1H), 0.94 & 0.93 (t, J=7.6 Hz, 3H); ¹³C NMR (100 MHz, CDCl₃) δ 167.11 & 166.89, 143.70 & 143.67, 132.25 & 132.16, 131.99 & 131.66, 129.49 & 129.41, 123.31 & 123.14, 123.13 & 123.00, 81.44 & 79.99, 57.38 & 55.98, 52.06 & 51.99, 49.39 & 51.77, 48.36 & 44.27, 27.35 & 27.54, 12.44 & 12.52; mass spectrometry: ESI-MS m/z 247.0 (M+H)⁺, HRMS calcd for C₁₄H₁₉N₂O₂ (M+H)⁺ m/z 247.1441. found 247.1444. Specific rotation: $[\alpha]_D^{24}$=+4.5 (c=1.33 in CHCl₃).

Embodiment 22

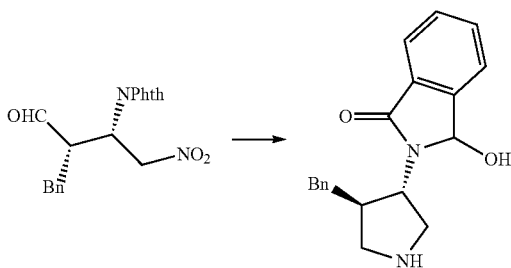

The reactants (0.20 mmol) was dissolved in H₂O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 with 4M aqueous NaOH solution after filtering. The solution was extracted by CH₂Cl₂ (3*10 mL), washed by brine, dried by anhydrous Na₂SO₄, The product was given after removing the solvent. Yield: 99%. The purity is showed greater than 95% by 1H NMR. The product with higher purity can be obtained by column chromatography. Eluent (AcOEt/(MeOH/NH₃)=12:1-8:1). NMR analysis: ¹H NMR (400 MHz, CDCl₃) δ 7.75-7.73 (m, 1H), 7.55-7.52 (m, 2H), 7.48-7.44 (m, 1H), 7.27-7.21 (m, 2H), 7.19-7.14 (m, 3H), 5.93 & 5.73 (s, 1H), 4.83 & 4.37 (d & s, J=4.8 Hz, 1H), 4.61 (br, 2H), 3.36-3.31 (m, 1H), 3.21-3.09 (m, 1.5H), 3.03-2.99 (m, 2H), 2.81-2.80 (m, 0.5H), 2.67-2.59 (m, 2.5H), 2.47-2.43 (m, 0.5H); ¹³C NMR (100 MHz, CDCl₃) δ 167.39 & 167.11, 144.05 & 143.86, 139.74 & 139.23, 132.22 & 132.08, 132.00 & 131.51, 129.49 & 129.45, 128.87 & 128.73, 128.62 & 128.53, 126.50 & 126.32, 123.31 & 123.13, 123.13 & 122.97, 81.72 & 80.26, 57.62 & 56.28, 52.14 & 51.67, 51.42 & 49.86, 47.17 & 43.57, 39.96 & 39.62; mass spectrometry: ESI-MS m/z 309.2 (M+H)⁺, HRMS calcd for C₁₉H₂₁N₂O₂ (M+H)⁺ m/z 309.1597. found 309.1607; specific rotation: $[\alpha]_D^{24}$=+26.6 (c=1.1 in CHCl₃).

Embodiment 23

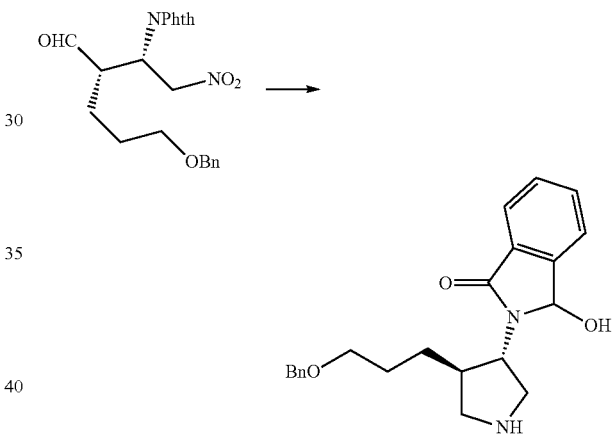

The reactants (0.20 mmol) was dissolved in H₂O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The value of pH was adjusted to 12 by 4M aqueous NaOH solution after filtering. The solution was extracted by CH₂Cl₂ (3*10 mL), washed by brine, dried by anhydrous Na₂SO₄. The product was given after removing the solvent. Yield: 99%. The purity is showed greater than 95% by 1H NMR. The product with higher purity can be obtained by column chromatography. Eluent (AcOEt/(MeOHNH₃)=12:1-8:1). NMR analysis: ¹H NMR (400 MHz, CDCl₃) δ 7.68-7.65 (m, 1H), 7.47-7.46 (m, 2H), 7.40-7.38 (m, 1H), 7.24-7.16 (m, 5H), 5.96 & 5.82 (s, 1H), 5.00 (br s, 2H), 4.62 & 4.40 (s, 1H), 4.38 & 4.29-4.24 (m, 2H), 3.39-3.35 (m, 2.5H), 3.28-3.26 (m, 1H), 2.98-2.95 (m, 0.5H), 2.92-2.80 (m, 1H), 2.41-2.37 & 2.30-2.29 & 2.21-2.18 (m, 2H), 1.71-1.67 (m, 1H), 1.61-1.39 (m, 4H); ¹³C NMR (100 MHz, CDCl₃) δ 167.04 & 166.84, 143.62 & 143.57, 138.66 & 138.50, 132.32 & 132.16, 131.97 & 131.71, 129.52 & 129.44, 128.44 & 127.72, 127.64 & 127.58, 123.38 & 123.18, 123.13 & 123.08, 81.15 & 79.89, 72.97 & 72.96, 70.34 & 69.90, 57.29 & 56.02, 52.38 & 52.17, 52.12 & 49.21, 46.97 & 42.27, 31.54 & 31.44, 28.21; mass spectrometry: ESI-MS m/z 367.2

(M+H)+, HRMS calcd for $C_{22}H_{27}N_2O_3$ (M+H)+ m/z 367.2016. found 367.2024; specific rotation: $[\alpha]_D^{24}=-5.5$ (c=1.1 in CHCl₃).

Embodiment 24

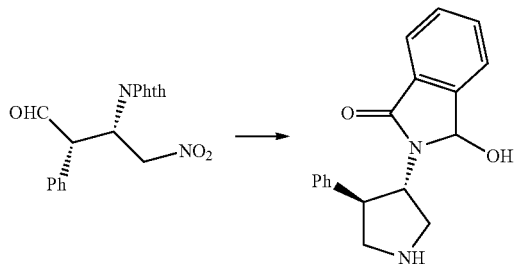

The reactants (0.20 mmol) was dissolved in H₂O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 by 4M aqueous NaOH solution after filtering. The solution was extracted by CH₂Cl₂ (3*10 mL), washed by brine, dried by anhydrous Na₂SO₄. The product was given after removing the solvent. Yield: 99%. The purity is showed greater than 95% by ¹H NMR. The product with higher purity can be obtained by column chromatography. Eluent (AcOEt/(MeOH/NH₃)=12:1-8:1). NMR analysis: ¹H NMR (400 MHz, CDCl₃) δ 7.74-7.73 (m, 1H), 7.56-7.53 (m, 2H), 7.50-7.44 (m, 1H), 7.30-7.26 (m, 2H), 7.22-7.19 (m, 3H), 5.99 & 5.71 (s, 1H), 5.00 (br s, 2H), 4.92-4.88 & 4.42-4.38 (m, 1H), 3.70-3.61 (m, 0.5H), 3.60-3.56 (m, 0.5), 3.53-3.48 (m, 0.5H), 3.41-3.36 (m, 1H), 3.12-3.11 (m, 1H), 3.04 (dd, J=7.6, 11.6, 0.5H), 2.81 & 2.65 (dd, J=8.8, 10.8, & 10.0, 11.2, 1H); ¹³C NMR (100 MHz, CDCl₃) δ 167.26 & 167.17, 144.24 & 144.08, 141.86 & 141.48, 132.32 & 132.20, 132.20 & 131.68, 129.65 & 129.61, 128.97 & 28.85, 127.51 & 127.43, 127.05 & 126.89, 123.42 & 123.23, 123.23 & 123.19, 82.32 & 80.70, 60.75 & 58.58, 54.23, 52.87 & 51.49, 50.54 & 48.10; mass spectrometry: ESI-MS m/z 295.0 (M+H)+, HRMS calcd for $C_{18}H_{18}N_2O_2Na$ (M+Na)+ m/z 317.1260. found 313.1262; specific rotation: $[\alpha]_D^{24}=-68.7$ (c=1.4 in CHCl₃).

Embodiment 25

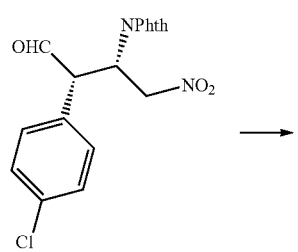

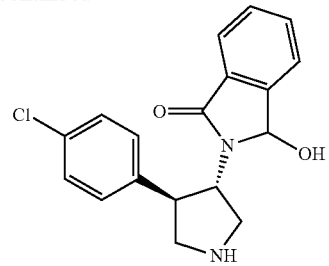

The reactants (0.20 mmol) was dissolved in H₂O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 by 4M aqueous NaOH solution after filtering. The solution was extracted by CH₂Cl₂ (3*10 mL), washed by brine, dried by anhydrous Na₂SO₄. The product was given after removing the solvent. Yield: 99%. The purity is showed greater than 95% by ¹H NMR. The product with higher purity can be obtained by column chromatography. Eluent (AcOEt/(MeOH/NH₃)=12:1-8:1). NMR analysis: ¹H NMR (400 MHz, CDCl₃) δ 7.75-7.73 (m, 1H), 7.57-7.55 (m, 2H), 7.51-7.45 (m, 1H), 7.28-7.26 (m, 2H), 7.22-7.20 (m, 1H), 6.02 & 5.87 (s, 1H), 4.93-4.90 & 4.51-4.48 (m, 1H), 4.60 (br s, 2H), 3.66-3.62 (m, 1H), 3.61-3.55 (m, 0.5H), 3.52-3.44 (m, 1H), 3.22-3.19 (m, 0.5H), 3.17-3.11 (m, 1H), 2.86 & 2.76 (dd, J=8.4, 9.6 & 9.2, 10.8); ¹³C NMR (100 MHz, CDCl₃) δ 167.34 & 167.13, 143.87 & 143.71, 140.58 & 140.20, 132.90 & 132.70, 132.44 & 132.32, 132.11 & 131.61, 129.78 & 129.73, 129.13 & 129.01, 128.96 & 128.82, 123.51 & 123.29, 81.87 & 80.54, 60.27 & 58.53, 54.24 & 53.89, 53.06 & 51.41, 50.24 & 47.76; mass spectrometry: ESI-MS m/z 329.0 (M+H)+, HRMS calcd for $C_{18}H_{18}ClN_2O_2$ (M+H)+ m/z 329.1051. found 329.1056; specific rotation: $[\alpha]_D^{24}=-68.2$ (c=1.2 in CHCl₃).

Embodiment 26

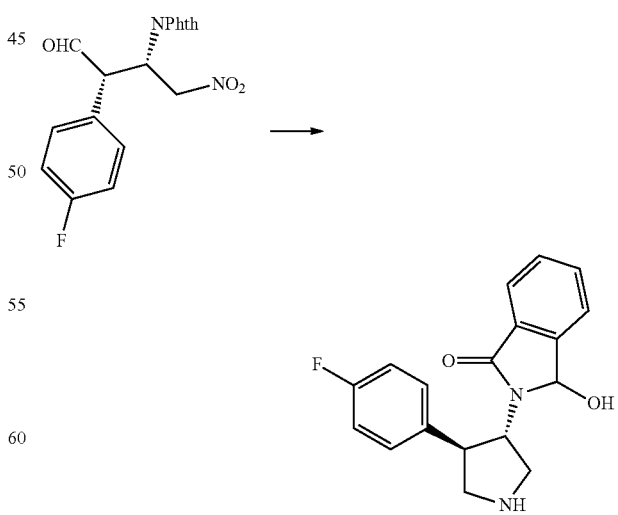

The reactant (0.20 mmol) was dissolved in H₂O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 by 4M aqueous NaOH solution after filtering. The solution was extracted by $CH_2Cl_2$ (3*10 mL), washed by brine, dried by anhydrous $Na_2SO_4$. The product was given after removing the solvent. Yield: 99%. The purity is showed greater than 95% by 1H NMR. The product with higher purity can be obtained by column chromatography. Eluent (AcOEt/(MeOH/NH$_3$)=12:1-8:1). NMR analysis: $^1$H NMR (400 MHz, CDCl$_3$) δ 7.70-7.67 (m, 1H), 7.54-7.51 (m, 2H), 7.48-7.44 (m, 1H), 7.16-7.15 (m, 2H), 6.18-6.94 (m, 2H), 5.96 & 5.69 (s, 1H), 5.46 (br, 2H), 4.83 & 4.38 (m, 1H), 3.72-3.59 (m, 1H), 3.50-3.46 & 3.07-3.02 (m, 1H), 3.40-3.38 (m, 1H), 3.16-3.12 (m, 1H), 2.75 & 2.63 (t, J=10.0, 1H); $^{19}$F NMR (300 MHz, CDCl$_3$) δ −116.06 & −116.44; $^{13}$C NMR (100 MHz, CDCl$_3$) δ 167.42 & 167.33, 161.90 & 161.86 (d, J=245 Hz), 144.13 & 144.03, 137.01 & 136.51 (d, J=3.0 Hz), 132.44 & 132.34, 131.98 & 131.45, 129.71 & 129.67, 128.99 & 128.93 (J=8.1 Hz), 123.37 & 123.27, 123.29 & 123.15, 115.82 & 115.71 (d, J=21 Hz), 82.34 & 80.78, 60.57 & 58.38, 53.98 & 53.85, 52.15 & 50.23, 50.02 & 47.23; mass spectrometry: ESI-MS m/z 313.0 (M+H)$^+$, HRMS calcd for $C_{18}H_{18}FN_2O_2$ (M+H)$^+$ m/z 313.1346. found 313.1352; specific rotation: [α]$_D^{24}$=−68.9 (c=0.9 in CHCl$_3$).

Embodiment 27

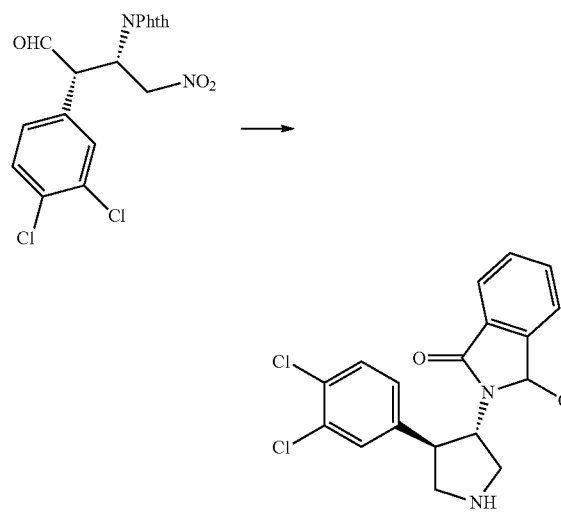

The reactant (0.20 mmol) was dissolved in H$_2$O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 by 4M aqueous NaOH solution after filtering. The solution was extracted by $CH_2Cl_2$ (3*10 mL), washed by brine, dried by anhydrous $Na_2SO_4$. The product was given after removing the solvent. Yield: 99%. The purity is showed greater than 95% by 1H NMR. The product with higher purity can be obtained by column chromatography. Eluent (AcOEt/(MeOH/NH$_3$)=12:1-8:1). NMR analysis: $^1$H NMR (400 MHz, CDCl$_3$) δ 7.73-7.72 (m, 1H), 7.57-7.56 (m, 2H), 7.50-7.47 (m, 1H), 7.40-7.34 (m, 2H), 7.21-7.19 & 7.11-7.09 (m, 1H), 6.04 & 5.95 (s, 1H), 5.47 (d, J=18.8 Hz, 1H), 5.00 (br s, 1H), 4.97 & 4.61 (s, 1H), 3.75-3.71 (m, 1H), 3.68-3.56 (m, 1.5H), 3.36-3.25 (m, 1.5H), 2.96-2.89 (m, 1H); $^{13}$C NMR (100 MHz, CDCl$_3$) δ 172.67, 167.50 & 167.27, 143.71 & 143.61, 141.97 & 141.44, 133.00 & 132.84, 132.59 & 132.47, 131.88 & 131.41, 131.35 & 131.11, 131.00 & 130.88, 129.86 & 129.82, 129.54 & 129.46, 127.38 & 126.97, 123.53 & 123.38, 123.38 & 123.31, 81.69 & 80.56, 59.65 & 58.08, 53.82 & 53.34, 52.51 & 50.81, 49.78 & 47.39, 22.73; mass spectrometry: ESI-MS m/z 363.0 (M+H)$^+$, HRMS calcd for $C_{18}H_{17}Cl_2N_2O_2$ (M+H)$^+$ m/z 363.0661. found 363.0670; specific rotation: [α]$_D^{24}$=−53.5 (c=1.0 in CHCl$_3$).

Embodiment 28

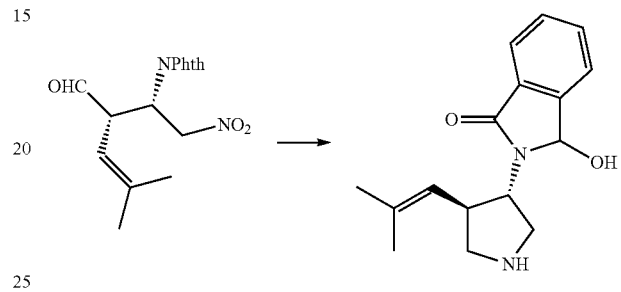

The reactant (0.20 mmol) was dissolved in H$_2$O/AcOH (1:1; 4 mL), activated zinc powder (325 mg, 5 mmol, 25 equiv.) was added in batches within 10 min at 0° C., the temperature was raised to room temperature naturally, and the reaction mixture was stirred for 2-7 h. The pH value was adjusted to 12 by 4M aqueous NaOH solution after filtering. The solution was extracted by $CH_2Cl_2$ (3*10 mL), washed by brine, dried by anhydrous $Na_2SO_4$. The product was given after removing the solvent. Yield: 99%. The purity is showed greater than 95% by 1H NMR. The product with higher purity can be obtained by column chromatography. Eluent (AcOEt/(MeOH/NH$_3$)=12:1-8:1). NMR analysis: $^1$H NMR (400 MHz, CDCl$_3$) δ 7.78-7.76 (m, 1H), 7.60-7.54 (m, 2H), 7.51-7.46 (m, 1H), 6.03 (s, 1H), 5.16-5.10 (m, 1H), 4.74-4.73 & 4.35-4.33 (m, 1H), 3.59-3.54 (m, 0.5H), 3.47-3.41 (m, 0.5H), 3.39-3.37 (m, 0.5H), 3.30-3.28 (m, 0.5H), 3.18-3.16 (m, 0.5H), 3.14-3.10 (m, 1H), 3.05-3.01 (m, 0.5H), 2.66-2.61 (m, 0.5H), 2.56-2.51 (m, 0.5H), 1.71 & 1.70 (s, 3H), 1.62 & 1.58 (s, 3H); $^{13}$C NMR (100 MHz, CDCl$_3$) δ 167.17 & 167.01, 143.70, 134.42 & 134.16, 132.33 & 131.74, 132.26 & 132.09, 129.63 & 129.53, 126.05 & 125.49, 123.53 & 123.20, 123.25, 81.45 & 80.13, 58.89 & 57.89, 52.58 & 52.55, 52.42 & 49.30, 45.52 & 41.22, 25.98 & 25.73, 18.48 & 18.40; mass spectrometry: ESI-MS m/z 273.1 (M+H) HRMS calcd for $C_{16}H_{21}N_2O_2$ (M+H)$^+$ m/z 273.1597. found 273.1598; specific rotation: [α]$_D^{24}$=−14.0 (c=1.0 in CHCl$_3$).

Embodiment 29

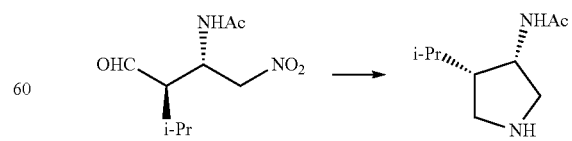

The reactant (0.20 mmol) was dissolved in 8 mL MeOH, 10% Pd(OH)$_2$/C (20% wt) was added at room temperature. The resultant mixture was stirred under hydrogen atmosphere at 1 atm for 2-12 h until the iminium intermediate was consumed. The catalyst was removed by filtering, the solvent was removed by vacuum evaporation and the residue was purified by column chromatography to get the product. The eluent is ethyl acetate: MeOH/NH$_3$=6:1-4:1. Yield: 95%. NMR analysis: $^1$H NMR (400 MHz, CDCl$_3$) δ 6.60 (d, J=9.2 Hz, 1H), 4.55 (quintet, J=4.8 Hz, 1H), 3.97 (br s, 1H), 3.20 (dd, J=8.8, 10.4 Hz, 1H), 2.92 (d, J=11.2 Hz, 1H), 2.72 (t, J=10.8 Hz, 1H), 1.99 (s, 3H), 1.83-1.75 (m, 1H), 1.58-1.51 (m, 1H), 0.97 (d, J=6.4 Hz, 3H), 0.90 (d, J=6.4 Hz, 3H); $^{13}$C NMR (100 MHz, CDCl$_3$) δ 169.96, 54.17, 51.01, 50.78, 48.66, 27.99, 23.45, 21.98, 21.92; mass spectrometry: ESI-MS m/z 171.1 (M+H)$^+$, HRMS calcd for C$_9$H$_{19}$N$_2$O (M+H)$^+$ m/z 171.1491. found 171.1493; specific rotation: $[α]_D^{24}$=−29.7 (c=1.1 in CHCl$_3$).

resultant mixture was stirred under hydrogen atmosphere at 5 atm for 48 h The solvent was removed by vacuum evaporation. The product was given by column chromatography (Eluent:dichloromethane/methanol=10:1). Yield: 99%. NMR analysis: $^1$H NMR (400 MHz, CDCl$_3$) δ 7.87-7.83 (m, 2H), 7.74-7.71 (m, 2H), 4.63 (m, 1H), 3.62 (t, J=8.4 Hz, 1H), 3.51-3.46 (m, 1H), 3.35 (m, 1H), 2.89 (t, J=8.4 Hz, 1H), 2.58 (m, 1H), 1.64-1.50 (m, 2H), 1.26 (m, 1H), 0.89 (t, J=7.2 Hz, 3H); mass spectrometry: MS (m/z) 244.2 (M$^+$).

Embodiment 32

Embodiment 30

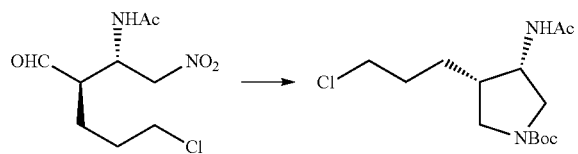 [SMILES: CC(=O)N[C@H](C[N+](=O)[O-])[C@H](C=O)CCCCl ; CC(=O)N[C@@H]1CN(C(=O)OC(C)(C)C)C[C@@H]1CCCCl]

The reactant (0.20 mmol) was dissolved in 8 mL of MeOH, 10% Pd/C (10% wt) was added at room temperature. The resultant mixture was stirred under hydrogen atmosphere at 1 atm for 2-12 h until the iminium intermediate was consumed. The catalyst was removed by filtering, and the solvent was removed by vacuum evaporation, 4 mL CH$_3$CN and Boc$_2$O (2 equiv.) were added. The mixture was stirred for 2 h and purified by column chromatography. The eluent is ethyl acetate: petroleum ether (2:1-3:1). Yield: 66%. NMR analysis: $^1$H NMR (400 MHz, CDCl$_3$) δ 5.74 (m, 1H), 4.56-4.58 (m, 1H), 3.65-3.50 (m, 4H), 3.32 (m, 1H), 3.01-2.92 (m, 1H), 2.27 (m, 1H), 2.02 (s, 3H), 1.86 (m, 1H), 1.77-1.74 (m, 1H), 1.52-1.46 (m, 2H), 1.46 (s, 9H); $^{13}$C NMR (100 MHz, CDCl$_3$) 170.05, 154.68, 79.96, 53.09 & 52.38 (due to rotamers), 50.92 & 50.17 (due to rotamers), 49.29 & 49.02 (due to rotamers), 45.12, 42.02 & 41.03 (due to rotamers), 30.88, 28.61, 25.03, 23.48; mass spectrometry: ESI-MS: [M+Na]$^+$ 327.2, [M+K]$^+$ 343.3. HRMS (EI) m/z calcd for C$_{14}$H$_{25}$ClN$_2$O$_3$ [M]$^+$ 304.1554, found 304.1556. HRMS (ESI) m/z calcd for C$_{14}$H$_{25}$ClN$_2$NaO$_3$ [M+Na]$^+$ 327.1446, found 327.1446; specific rotation: $[α]_D^{24}$=+16.98 (c=0.83 in CHCl$_3$).

Embodiment 31

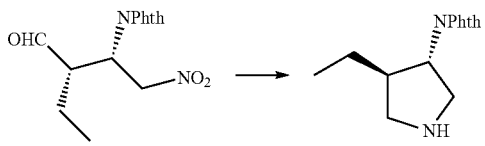

The reactant (1 mmol) was dissolved in 10 ml ethanol, Pd(OH)$_2$/C (10% wt of the reactant) was added, and the

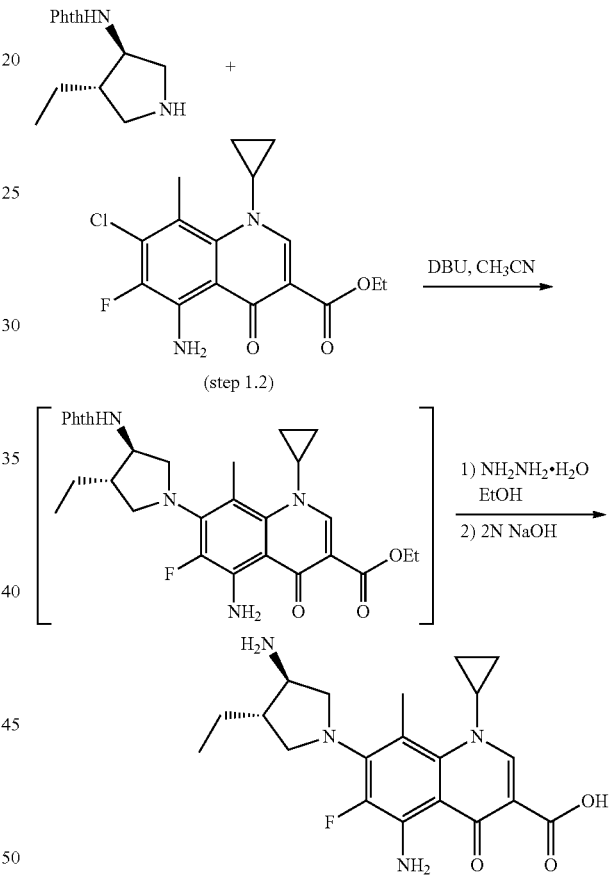

The reactant (1 mmol) was dissolved in 6 ml acetonitrile, RCl (4 mmol) and DBU (5 mmol) were added sequentially, the mixture was heated for 2 h at 70-75° C. After cooling and filtration, the solid was dissolved in 10 mL ethanol. Then hydrazine hydrate (100 mg, 2 mmol) was added and the reaction mixture was refluxed overnight. The mixture was cooled and carried on column chromatography. The product was given after saponification by 2N NaOH. Yield: 60%. NMR analysis: NMR (300 MHz, CDCl$_3$) δ 8.61 (s, 1H), 7.05 (brs, 2H), 4.08-4.20 (m, 1H), 3.75-3.89 (m, 1H), 3.60 (d, J=10.0 Hz, 1H), 3.42 (d, J=10.0 Hz, 1H), 3.01-3.32 (m, 2H), 2.35 (m, 3H), 1.04-1.20 (m, 2H), 0.38-0.90 (m, 6H); mass spectrometry: MS (m/z) 389.2 (M+H$^+$).

Embodiment 33

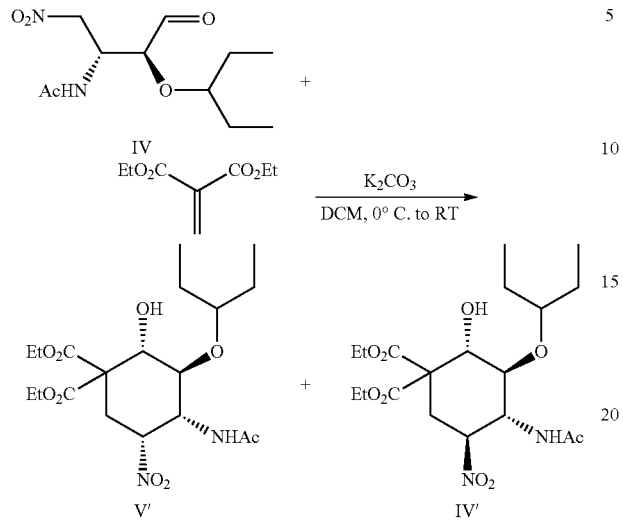

Aldehyde IV (1 mmol) and ethyl 2-ethoxy carbonyl acrylate (1.2 mmol) were dissolved in MeCN (2 mL), cooled down to 0° C. and potassium carbonate (1 mmol) was added, the reaction mixture was stirred for 3 hours. The reaction temperature was warmed to room temperature. Insolubles was removed by filtration after the reaction finished, the solvent was removed by vacuum evaporation, compound V' (Yield 17%) and IV' (Yield 43%) were given by column chromatography.

Compound V': NMR analysis: 1H NMR (400 MHz, CDCl$_3$): δ=6.88 (d, J=10.0 Hz, 1H), 5.38 (dt, J=12.8, 4.0 Hz, 1H), 5.09 (m, 1H), 4.62 (brd, 1H), 4.54 (d, J=2.4 Hz, 1H), 4.31-4.18 (m, 3H), 4.08-4.00 (m, 1H), 3.74 (t, J=3.2 Hz, 1H), 3.44-3.38 (m, 1H), 2.69 (dd, J=10.0, 4.0 Hz, 1H), 2.48 (t, J=12.8 Hz, 1H), 1.92 (s, 3H), 1.57-1.33 (m, 4H), 1.28 (t, J=7.2 Hz, 3H), 1.24 (t, J=7.2 Hz, 3H), 0.93 (t, J=7.6 Hz, 3H), 0.82 (t, J=7.6 Hz, 3H). $^{13}$C NMR (100 MHz, CDCl$_3$): δ=171.75, 169.92, 167.12, 82.52, 79.00, 75.46, 71.57, 62.96, 62.07, 56.83, 48.29, 26.30, 25.37, 23.79, 23.47, 13.97, 13.92, 10.07, 8.65; mass spectrometry: ESI-MS: [M+H]+ 433.5, [M+Na]+ 455.5, [M+MeOH+Na]+ 487.6; HRMS (ESI) m/z calcd for C$_{19}$H$_{32}$N$_2$O$_9$Na [M+Na]+ 455.2000. found 455.2019; $[\alpha]_D^{20.7}$ −10.0 (c=0.66, CHCl$_3$).

IV': NMR analysis: $^1$H NMR (400 MHz, CDCl$_3$): δ=5.78 (d, J=9.2 Hz, 1H), 5.35-5.26 (m, 1H), 5.09 (m, 1H), 4.62 (m, 1H), 4.39 (dd, J=14.0, 3.6 Hz, 1H), 4.35-4.19 (m, 4H), 3.93-3.84 (m, 1H), 3.35 (m, 1H), 2.81 (s, 1H), 2.74-2.71 (m, 2H), 1.93 (s, 3H), 1.59-1.43 (m, 4H), 1.31 (t, J=9.6 Hz, 3H), 1.26 (t, J=9.6 Hz, 3H), 0.91 (t, J=9.6 Hz, 3H), 0.86 (t, J=9.6 Hz, 3H). $^{13}$C NMR (100 MHz, CDCl$_3$): δ=171.27, 167.75, 167.72, 82.23, 81.95, 72.82, 69.74, 62.74, 62.59, 57.63, 53.50, 29.38, 26.24, 25.55, 23.71, 14.09, 14.07, 9.70, 9.29; mass spectrometry: ESI-MS: [M+H]$^+$ 433.4, [M+Na]$^+$ 455.4, [M+MeOH+Na]$^+$ 487.5; HRMS (ESI) m/z calcd for C$_{19}$H$_{32}$N$_2$O$_9$Na [M+Na]$^+$ 455.2000, found 455.2014; $[\alpha]_D^{20.7}$ −1.9 (c=0.66, CHCl$_3$).

Embodiment 34

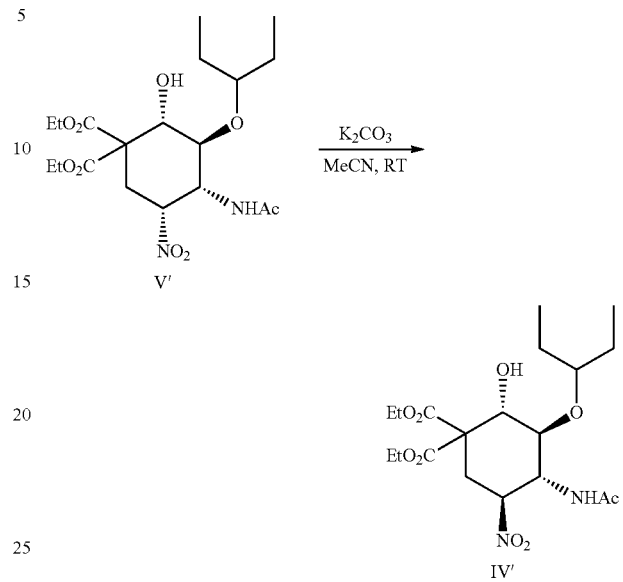

Compound V' was dissolved in acetonitrile, then potassium carbonate was added and the reaction mixture was stirred for 24 h at room temperature till the reaction finished. The compound IV' was given after removing the insoluble substance and the solvent by vacuum evaporation.

Compound IV', NMR analysis: $^1$H NMR (400 MHz, CDCl$_3$): δ=5.78 (d, J=9.2 Hz, 1H), 5.35-5.26 (m, 1H), 5.09 (m, 1H), 4.62 (m, 1H), 4.39 (dd, J=14.0, 3.6 Hz, 1H), 4.35-4.19 (m, 4H), 3.93-3.84 (m, 1H), 3.35 (m, 1H), 2.81 (s, 1H), 2.74-2.71 (m, 2H), 1.93 (s, 3H), 1.59-1.43 (m, 4H), 1.31 (t, J=9.6 Hz, 3H), 1.26 (t, J=9.6 Hz, 3H), 0.91 (t, J=9.6 Hz, 3H), 0.86 (t, J=9.6 Hz, 3H). $^{13}$C NMR (100 MHz, CDCl$_3$): δ=171.27, 167.75, 167.72, 82.23, 81.95, 72.82, 69.74, 62.74, 62.59, 57.63, 53.50, 29.38, 26.24, 25.55, 23.71, 14.09, 14.07, 9.70, 9.29; mass spectrometry: ESI-MS: [M+H]$^+$ 433.4, [M+Na]$^+$ 455.4, [M+MeOH+Na]$^+$ 487.5; HRMS (ESI) m/z calcd for C$_{19}$H$_{32}$N$_2$O$_9$Na [M+Na]$^+$ 455.2000, found 455.2014; $[\alpha]_D^{20.7}$ −1.9 (c=0.66, CHCl$_3$).

Embodiment 35

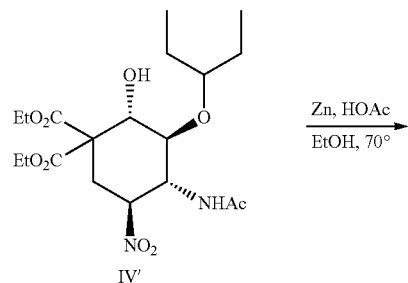

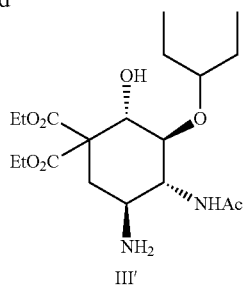

III'

Compound IV' (0.21 mmol) was dissolved in ethanol (2 mL), zinc powder (3.15 mmol) was added, the mixture was heated to 70° C. under argon atmosphere, and then acetic acid (1 mL) was added, stirred and reacted for 30 min till the reaction finished. The reaction mixture was cooled to room temperature. The solution was adjusted to alkalinity by aqueous ammonia, extracted by 10% MeOH/CHCl$_3$ (volume ratio) for 3 times. The obtained organic phase was washed by brine for 1 time, dried with anhydrous sodium sulfate. The compound III' was given after filtering desiccant and removing the solvent by vacuum evaporation (90%).

Compound III': mass spectrometry: ESI-MS: [M+H]$^+$ 403.7, [M+Na]$^+$ 425.3; HRMS (ESI) m/z calcd for C$_{19}$H$_{35}$N$_2$O$_7$Na [M+H]$^+$ 403.2439, found 403.2449

Embodiment 36

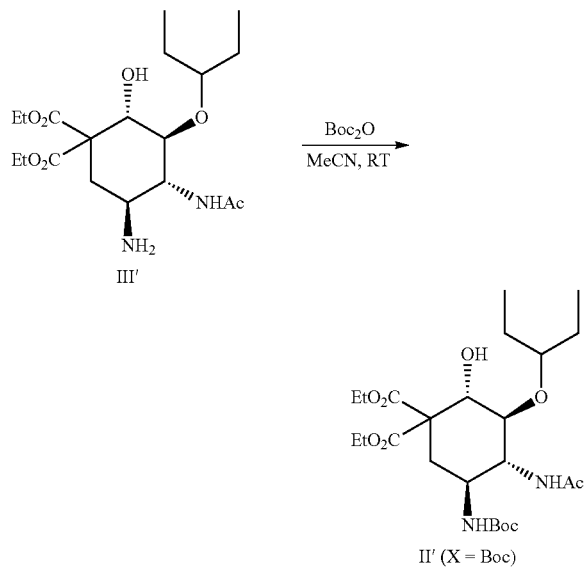

Compound III' (0.074 mmol) was dissolved in acetonitrile (1.5 mL), Boc$_2$O (0.148 mmol) was added at room temperature. The reaction mixture was stirred for 4 h till the substrate was completely transformed. The solvent was removed by vacuum evaporation, and the crude product can be used for the next step directly. Compound II' (X is Boc) was given (83% for 2 steps) by column chromatography.

Compound II' (X=Boc): NMR analysis: $^1$H NMR (400 MHz, CDCl$_3$): δ=5.54 (d, J=10.0 Hz, 1H), 4.76 (d, J=8.4 Hz, 1H), 4.49 (m, 1H), 4.29-4.18 (m, 4H), 4.08 (q, J=10.4 Hz, 1H), 3.66 (dd, J=10.4, 2.0 Hz, 1H), 3.35 (m, 1H), 2.78 (m, 1H), 2.34-2.21 (m, 2H), 1.94 (s, 3H), 1.56-1.48 (m, 4H), 1.40 (s, 9H), 1.28-1.23 (m, 6H), 0.91-0.84 (m, 6H); $^{13}$C NMR (100 MHz, CDCl$_3$): 171.03, 169.41, 168.31, 156.29, 82.37, 79.79, 69.76, 62.14, 62.06, 57.88, 53.18, 49.34, 31.07, 28.44, 27.62, 26.16, 25.61, 23.60, 14.12, 14.07, 9.83, 8.99; mass spectrometry: ESI-MS: [M+H]$^+$ 503.3, [M+Na]$^+$ 523.3; HRMS (ESI) m/z calcd for C$_{24}$H$_{42}$N$_2$O$_9$Na [M+Na]$^+$ 525.2782, found 455.2799; specific rotation: [α]$_D^{20.7}$ −21.9 (c=0.28, CHCl$_3$).

Embodiment 37

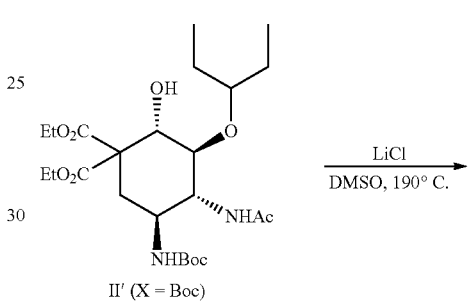

II' (X = Boc)

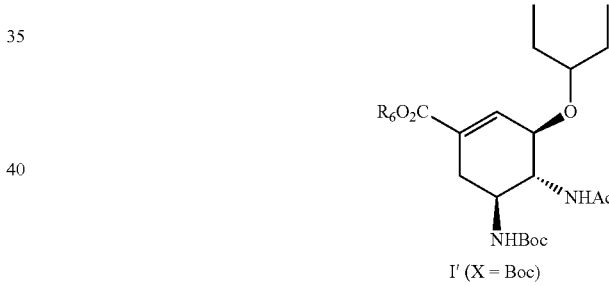

I' (X = Boc)

Compound II' (X=Boc) (0.031 mmol) was dissolved in dimethyl sulfoxide (1.5 mL), lithium chloride (0.031 mmol) was added, the mixture was heated to 190° C. under argon atmosphere and reacted for 2 h till the substrate had been completely transformed. The mixture was cooled to room temperature, the reaction mixture was added into brine in dropwise, and extracted with ethyl ether for 3 times. The obtained organic phase was dried with anhydrous sodium sulfate, and the compound I' (X=Boc) was given after column chromatography (79%).

Compound I' (X=Boc): NMR analysis: NMR analysis: $^1$H NMR (400 MHz, CDCl$_3$): δ=6.80 (s, 1H), 5.68 (d, J=8.4 Hz, 1H), 5.06 (d, J=9.2 Hz, 1H), 4.22 (q, J=7.2 Hz, 2H), 4.06 (t, J=9.2 Hz, 1H), 3.95 (m, 1H), 3.81-3.78 (m, 1H), 3.35 (m, 1H), 2.74 (dd, J=18.0, 4.8 Hz, 1H), 2.30 (m, 1H), 1.98 (s, 3H), 1.53-1.48 (m, 4H), 1.42 (s, 9H), 1.28-1.23 (m, 3H), 1.27 (t, J=7.0 Hz, 3H), 0.92-0.86 (m, 6H); mass spectrometry: ESI-MS: [M+H]$^+$ 413.3, [M+Na]$^+$ 435.3; HRMS (ESI) m/z calcd for C$_{21}$H$_{36}$N$_2$O$_6$Na [M+Na]$^+$ 435.2466, found 435.2485; specific rotation: [α]$_D^{20.7}$ −93.6.

Embodiment 38

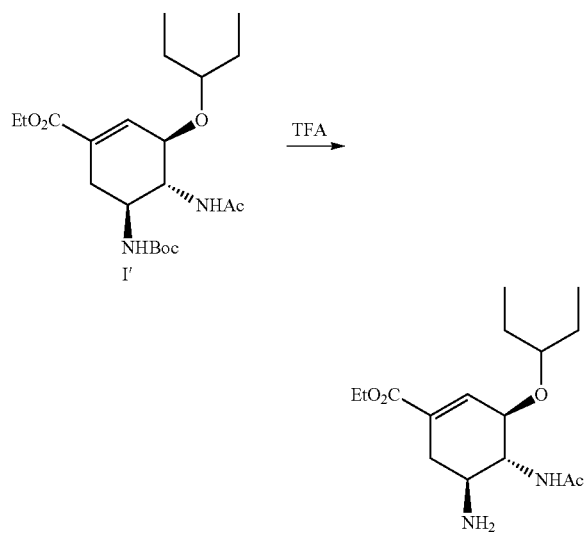

The reactant was dissolved in dichloromethane (1 mL), TFA (50 mmol) was added under the protection of argon at room temperature. The reaction mixture was stirred for 4 h at room temperature and then pH value of the mixture was adjusted to 12 by aqueous ammonia. The mixture was extracted by chloroform for three times, the organic phase was washed by brine, dried by anhydrous magnesium sulfate. The solvent was removed by vacuum evaporation and the product was given. Yield: 92%. Spectral analysis data is according to embodiment 19.

What is claimed is:

1. A chiral amino compound having a structure represented by a formula selected from the group consisting of:

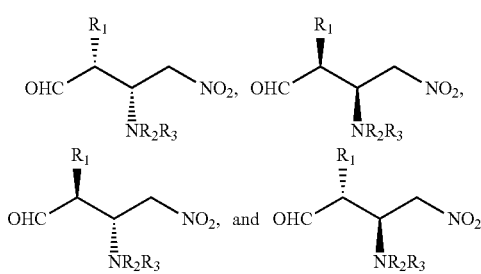

wherein:
$R_1$ is an alkyl having 1-10 carbon atoms, an alkoxy having 1-10 carbon atoms, an alkenyl having 2-6 carbon atoms, an alkyl having 1-4 carbon atoms and substituted by $R_4$, an aryl having 5-12 carbon atoms, or an aryl having 5-12 carbon atoms and monosubstituted or multisubstituted by an electron-withdrawing group or electron-donating group;

$R_4$ is a substituted amino, a hydroxyl, a substituted hydroxyl, an alkylacyloxy having 2-10 carbon atoms, or an alkenyl having 2-6 carbon atoms; the substituted amino comprising a substituent selected from the group consisting of: t-butoxycarboryl, benzyloxycarbonyl, benzyl, acetyl, trifluoromethyl carbonyl, and phthalyl;

the phthalyl having a structure represented by formula (a):

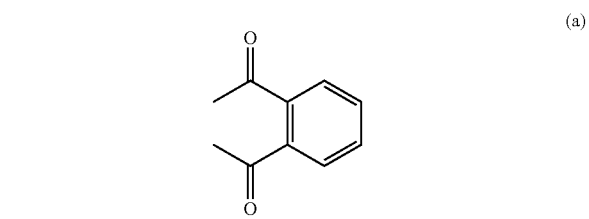

the substituted hydroxyl comprising a substituent selected from the group consisting of:
benzyl, acetyl, methoxymethyl, t-butyl dimethyl silyl, trimethylsilyl, triethylsilyl, t-butyldiphenylsilyl, and 2-tetrahydropyranyl; and
at least one of $R_2$ and $R_3$ is an acyl protecting group.

2. The chiral amino compound according to claim 1, wherein $R_1$ is an alkyl having 1-4 carbon atoms; an alkoxy having 1-4 carbon atoms; an alkyl having 1-4 carbon atoms and substituted by $R_4$; a phenyl; or a phenyl monosubstituted, disubstituted, or trisubstituted by an electron-withdrawing group or electron-donating group.

3. The chiral amino compound according to claim 2, wherein:
the electron-withdrawing group is a halogen, cyano, or nitro; and
the electron-donating group is an alkyl having 1-4 carbon atoms, an alkoxy having 1-4 carbon atoms, an amino, or a hydroxyl.

4. The chiral amino compound according to claim 1, wherein $R_1$ is an alkyl having 1-10 carbon atoms, 3-pentyloxy, isobutenyl, an alkyl having 1-4 carbon atoms and substituted by $R_4$, an aryl having 5-12 carbon atoms, or an aryl having 5-12 carbon atoms and monosubstituted or multisubstituted by an electron-withdrawing group or electron-donating group.

5. The chiral amino compound according to claim 1, wherein the structure is represented by a formula selected from the group consisting of:

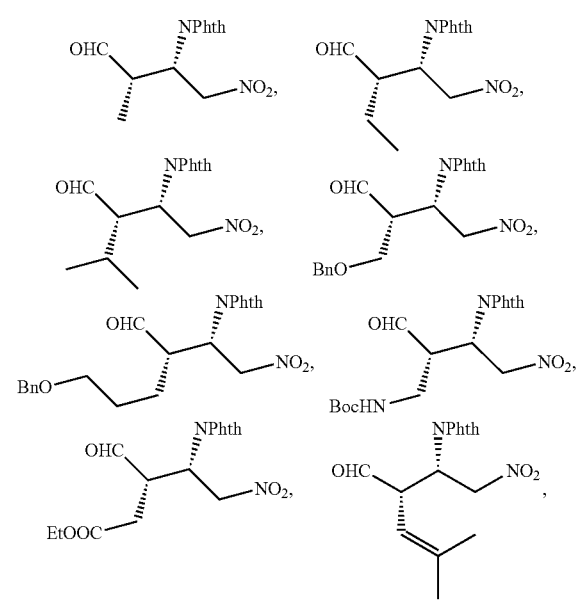

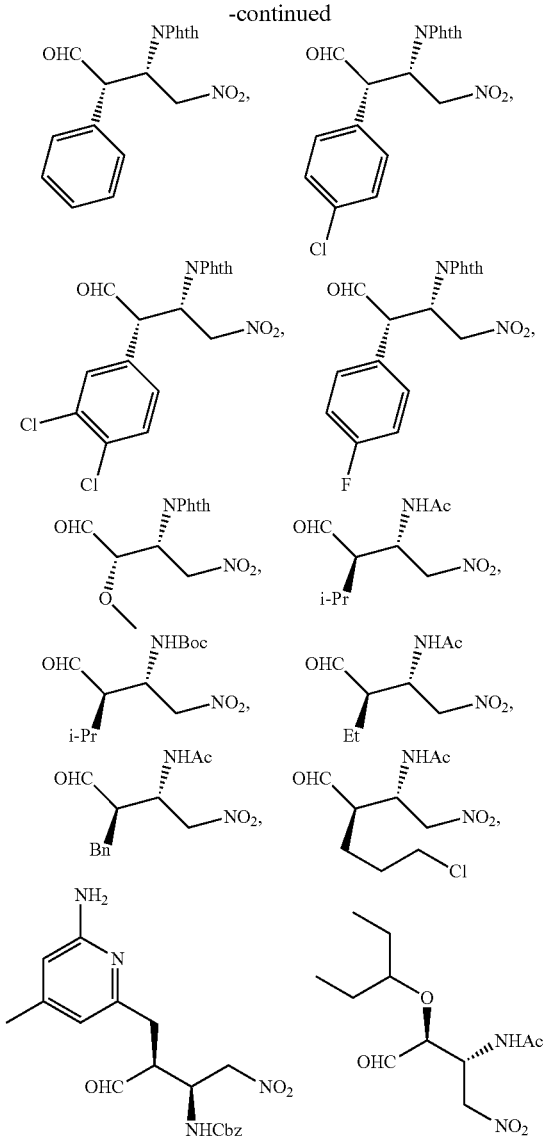

and enantiomers thereof,
where:
Boc represents t-butoxycarbonyl;
Bn represents benzyl;
Ac represents acetyl;
Phth represents phthalyl; and
Cbz represents benzyloxycarbonyl.

6. A method for preparing the chiral amino compound according to claim 1, comprising:
reacting an aldehyde represented by $R_1CH_2CHO$ and a nitroolefin represented by $O_2NCHCHNR_2R_3$ for 10 minutes to 48 hours in a solvent at 20 to 30° C. in the presence of a catalyst and an additive;
wherein:
the aldehyde, nitroolefin, catalyst, and additive have a molar ratio of: 1.0-4.0: 1.0-2.0:0.01-0.20:0-0.50;
the additive is one or more selected from the group consisting of acetic acid, chloroacetic acid, bromoacetic acid, sodium acetate, benzoic acid, and substituted benzoic acid; and the catalyst is:

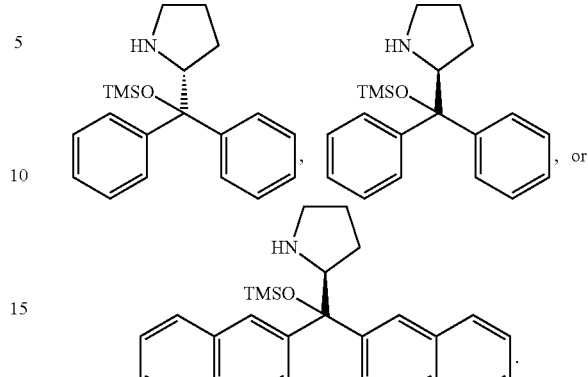

7. A method for preparing oseltamivir comprising:
(1) carrying out a reduction reaction of a nitro group of a compound represented by formula II to prepare a compound represented by formula I; and
(2) preparing oseltamivir by reacting the compound represented by formula I in the presence of an alkali, ammonia gas, and a solvent:

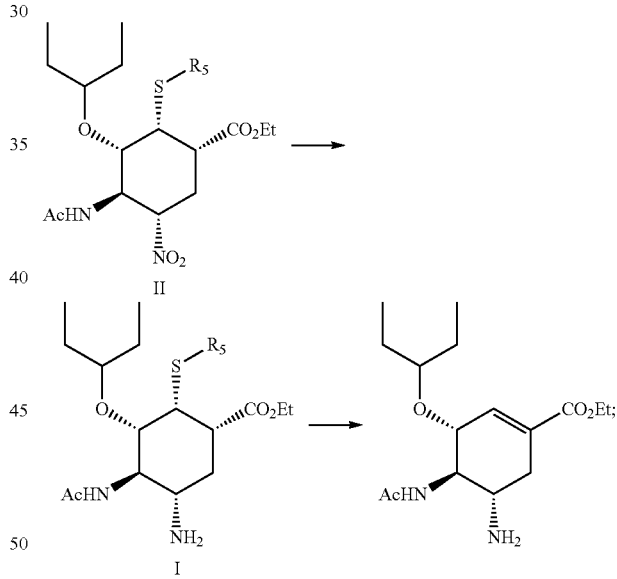

wherein:
$R_5$ is an unsubstituted, monosubstituted, or multisubstituted aryl having 6-12 carbon atoms, or an alkyl having 1-6 carbon atoms, the monosubstituted or multisubstituted aryl comprising a substituent selected from the group consisting of: a halogen, a nitro, an alkyl having 1-3 carbon atoms, and an alkoxy having 1-3 carbon atoms;

the compound represented by formula II is prepared by carrying out an addition reaction of a compound represented by formula III as follows:

57

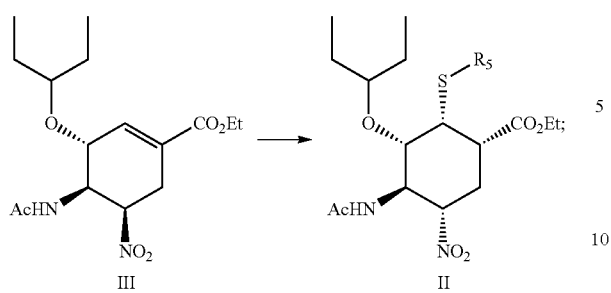

and
the compound represented by formula III is prepared by reacting a chiral amino compound represented by formula IV with ethyl 2-diethoxyphosphinoylacrylate:

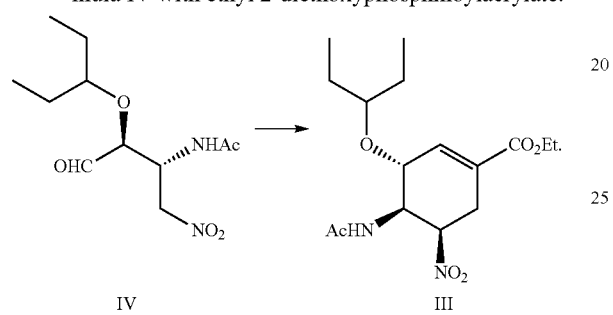

8. The method according to claim 7, wherein:
the reaction of the chiral amino compound represented by formula IV and ethyl 2-diethoxyphosphinoylacrylate is carried out in the presence of an alkali and a solvent;
the solvent is one or more selected from the group consisting of dichloromethane, chloroform, toluene, ethanol, and methanol;
the alkali is inorganic carbonate alkali or organic alkali;
the organic alkali is 1,8-diazabicycloundec-7-ene (DBU);
the inorganic carbonate alkali is cesium carbonate;
an amount of the alkali is 2-10 times an amount in moles of the compound represented by formula IV;
the reaction is stopped only once the chiral amino compound represented by formula IV is completely consumed; and
the reaction is carried out at a temperature of 10-30° C.

9. A method for preparing an intermediate compound of oseltamivir represented by formula I', the method comprising preparing the compound represented by formula I' by carrying out a reaction to remove an ester group and a hydroxyl group from a compound represented by formula II' in the presence of an inorganic salt, a solvent, and an inert:

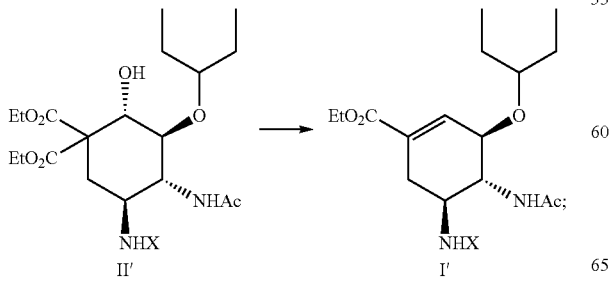

58 wherein:
X is an amino protecting group;
the inorganic salt is selected from the group consisting of sodium chloride, potassium chloride, and lithium chloride;
the solvent is selected from the group consisting of dimethylformamide, xylene, and dimethylsulfoxide;
the compound represented by formula II' is prepared by carrying out an amino protecting reaction of a compound represented by formula III':

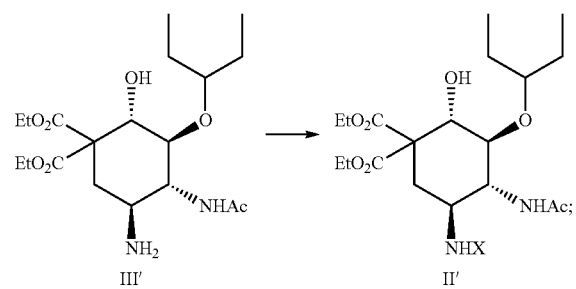

when X is t-butoxycarbonyl, the amino protecting reaction of the compounds represented by formula III' and di-tert-butyl dicarbonate ester ($Boc_2O$) in a solvent is carried out to provide the compound represented by formula II';
the solvent is one or more selected from the group consisting of dichloromethane, tetrahydrofuran, and acetonitrile;
an amount of di tert-butyl dicarbonate ester is 1-5 times an amount in moles of the compound represented by formula III';
the amino protecting reaction is carried out at a temperature of −20-50° C.;
the amino protecting reaction is stopped only once the compound represented by formula III' is completely consumed;
the compound represented by formula III' is prepared by carrying out a reduction reaction of a nitro group of a compound represented by formula IV':

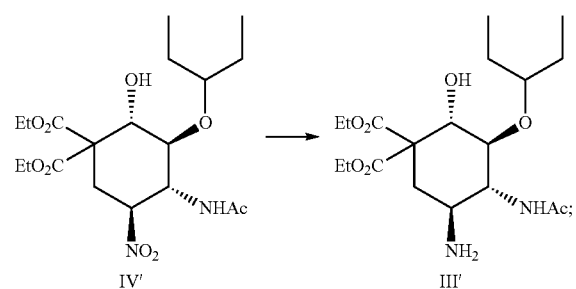

and
the compound represented by formula IV' is prepared by:
carrying out an isomerization reaction of a compound represented by formula V' in the presence of an alkali catalyst and a solvent:

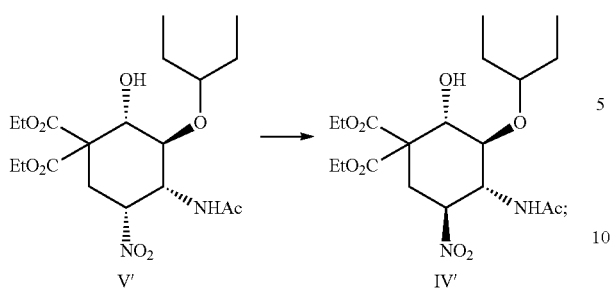

or
carrying out an intermolecular addition reaction and an intramolecular aldol reaction of a chiral amino compound represented by formula IV and ethyl 2-ethoxy carbonyl acrylate in the presence of an alkali catalyst and a solvent:

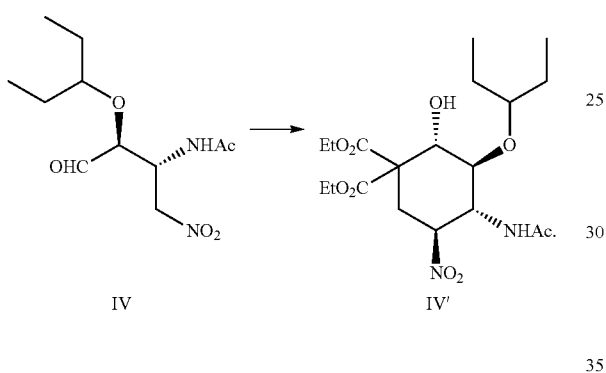

10. The method according to claim 9, wherein:
the solvent is one or more selected from the group consisting of dichloromethane, tetrahydrofuran, and acetonitrile;
the alkali catalyst is one or more selected from the group consisting of cesium carbonate, sodium carbonate, potassium phosphate, and potassium carbonate;
an amount of the alkali catalyst is 0.1-5 times an amount in moles of the compound represented by formula V';
the isomerization reaction is carried out at a temperature of −20-60° C.;
the reaction is stopped only once the compound represented by formula V' is completely consumed;
an amount of the alkali catalyst is 0.1-5 times an amount in moles of the chiral amino compound represented by formula IV;
a molar ratio of the chiral amino compound represented by formula IV and ethyl 2-ethoxy carbonyl acrylate is 0.1-1;
the intermolecular addition reaction and the intramolecular aldol reaction are carried out at a temperature of −20-50° C.; and
the intermolecular addition reaction and the intramolecular aldol reaction are stopped only once the chiral amino compound represented by formula IV is completely consumed.

11. The method according to claim 9, wherein:
the compound represented by formula V' is prepared by carrying out an intermolecular addition reaction and an intramolecular aldol reaction of the chiral amino compound represented by formula IV and ethyl 2-ethoxy carbonyl acrylate in the presence of an alkali catalyst and a solvent:

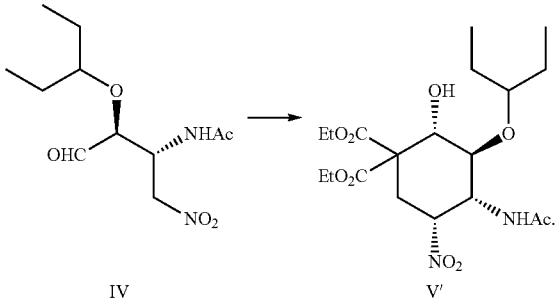

12. An intermediate compound for preparing oseltamivir having a structure represented by formula III, II, II', III', IV', or V':

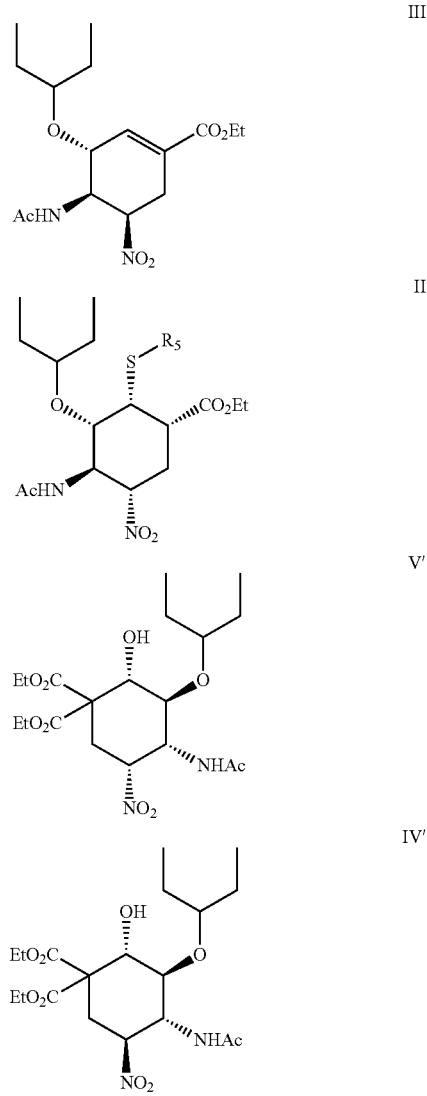

-continued

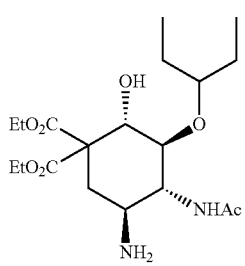

III'

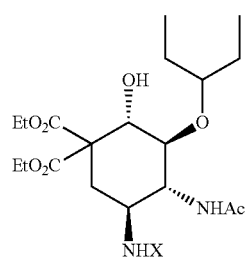

II' wherein:
R$_5$ is an unsubstituted, monosubstituted, or multi-substituted aryl having 6-12 carbon atoms, or an alkyl having 1-6 carbon atoms; the monosubstituted or multisubstituted aryl comprising a substituent selected from the group consisting of: a halogen, a nitro, an alkyl having 1-3 carbon atoms, and an alkoxy having 1-3 carbon atoms;
R$_5$ is not a tolyl; and
the intermediated compound represented by formula III, II, II', III', IV', or V' is prepared from the chiral amino compound according to claim 1.

13. A method for preparing a chiral 3-aminopyrrolidine represented by formula VI or formula VI', the method comprising carrying out a reduction reaction of a nitro group of the chiral amino compound according to claim 1 and a reductive amination reaction of the chiral amino compound; the chiral amino compound being represented by formula VII or formula VII':

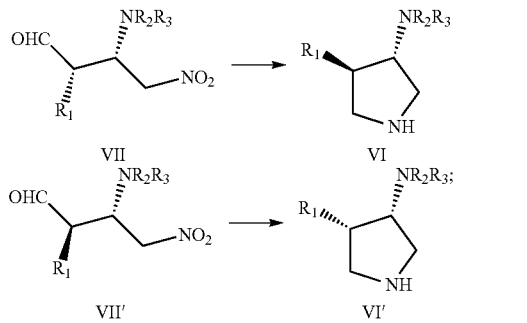

where:
R$_1$ is an alkyl having 1-10 carbon atoms, an alkoxy having 1-10 carbon atoms, an alkenyl having 2-6 carbon atoms, an alkyl having 1-4 carbon atoms and substituted by R$_4$, an aryl having 5-12 carbon atoms, or an aryl having 5-12 carbon atoms and monosubstituted or multisubstituted by an electron-withdrawing group or electron-donating group;
R$_4$ is a substituted amino, a hydroxyl, a substituted hydroxyl, an alkylacyloxy having 2-10 carbon atoms, or an alkenyl having 2-6 carbon atoms; the substituted amino comprising a substituent selected from the group consisting of: t-butoxycarboryl, benzyloxycarbonyl, benzyl, acetyl, trifluoromethyl carbonyl, and phthalyl; the phthalyl having a structure represented by formula (a):

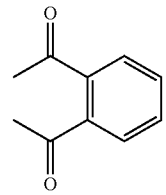

(a)

the substituted hydroxyl comprising a substituent selected from the group consisting of: benzyl, acetyl, methoxymethyl, t-butyl dimethyl silyl, trimethylsilyl, triethylsilyl, t-butyldiphenylsilyl, and 2-tetrahydropyranyl; and
at least one of R$_2$ and R$_3$ is an acyl protecting group.

14. The method according to claim 13, further comprising:
carrying out the reduction reaction of the nitro group and the reductive amination reaction of the chiral amino compound represented by formula VII or formula VII' in the presence of a catalyst and hydrogen in a polar solvent; the polar solvent being an alcohol solvent; the catalyst being Pd/C, Pd(OH)$_2$/C, PtO$_2$, or Ranny-Ni; a weight ratio of the chiral amino compound represented by formula VII or formula VII' to the catalyst being 1:0.001-0.2; a hydrogen pressure being $1 \times 10^5$ Pa to $100 \times 10^5$ Pa; the reaction being stopped only once the chiral amino compound represented by formula VII or formula VII' is completely consumed; the reduction reaction and the reductive amination reaction being carried out at a temperature of 0° C. to 100° C.; or
first carrying out the reduction reaction of the nitro group of the chiral amino compound represented by formula VII or formula VII', and then carrying out the reductive amination reaction; the reduction reaction of the nitro group of the chiral amino compound represented by formula VII or formula VII' being carried out in the presence of a reducing agent selected from the group consisting of Zn/HOAc, Fe powder, and Ranny-Ni/H$_2$ in a solvent;
wherein:
when the reducing agent is Zn/HOAc or Fe powder,
an amount of Zn or Fe powder is 10 to 30 times an amount in moles of the chiral amino compound represented by formula VII or formula VII';
the solvent is acetic acid or a mixture of acetic acid and water;
the reduction reaction is stopped only once the chiral amino compound represented by formula VII or formula VII' is completely consumed; and
the reduction reaction is carried out at a temperature of 0° C. to 100° C.;
when the reducing agent is Ranny-Ni/H$_2$,
a weight ratio of the chiral amino compound represented by formula VII or formula VII' to Ranny-Ni is 1:0.001-0.2;
a hydrogen pressure is $1 \times 10^5$ Pa to $100 \times 10^5$ Pa;
the solvent is an alcohol solvent;

the reduction reaction is stopped only once the chiral amino compound represented by formula VII or formula VII' is completely consumed; and the reduction reaction is carried out at a temperature of 0° C. to 100° C.;

the reductive amination reaction is carried out on substances obtained by the reduction reaction in the presence of a reducing agent in a solvent;

the solvent is one or more selected from the group consisting of dichloromethane, tetrahydrofuran, and 1,2-dichloromethane;

the reducing agent is sodium borohydride, sodium cyanoborohydride, acetic acid sodium borohydride, borane/pyridine, sodium borohydride/magnesium perchlorate, zinc borohydride/zinc chloride, or sodium triacetoxyborohydride;

an amount of the reducing agent is 1 to 4 times an amount in moles of the chiral amino compound represented by formula VII or formula VII';

the reductive amination reaction is stopped only once the substances prepared by the reduction reaction are completely consumed; and the reductive amination reaction is carried out at a temperature of 0° C. to 30° C.

15. The chiral amino compound according to claim 1, wherein the acyl protecting group is selected from the group consisting of t-butoxycarbonyl, benzyloxycarbonyl, acetyl, trifluoromethyl carbonyl, and phthalyl.

16. The chiral amino compound according to claim 1, wherein one of $R_2$ and $R_3$ is hydrogen or benzyl.

* * * * *